US009375488B2

(12) United States Patent
Balderes et al.

(10) Patent No.: US 9,375,488 B2
(45) Date of Patent: Jun. 28, 2016

(54) COMPOUNDS TO FIBROBLAST GROWTH FACTOR RECEPTOR-3 (FGFR3) AND METHODS OF TREATMENT

(71) Applicants: ImClone LLC, Indianapolis, IN (US); ImmunoGen, Inc., Waltham, MA (US)

(72) Inventors: Paul J. Balderes, New York, NY (US); Scott W. Eastman, New York, NY (US); Hans K. Erickson, Waltham, MA (US); Dale L. Ludwig, Denville, NJ (US); Christopher M. Moxham, Princeton Junction, NJ (US); Gregory D. Plowman, New York, NY (US); Alan C. Rigby, Glen Ridge, NJ (US)

(73) Assignees: ImClone, LLC, Indianapolis, IN (US); ImmunoGen, Inc., Waltham, MA (US)

( * ) Notice: Subject to any disclaimer, the term of this patent is extended or adjusted under 35 U.S.C. 154(b) by 0 days.

(21) Appl. No.: 14/567,063

(22) Filed: Dec. 11, 2014

(65) Prior Publication Data

US 2015/0165067 A1    Jun. 18, 2015

Related U.S. Application Data

(60) Provisional application No. 61/917,457, filed on Dec. 18, 2013, provisional application No. 61/928,025, filed on Jan. 16, 2014.

(51) Int. Cl.
| | | |
|---|---|---|
| *A61K 39/395* | (2006.01) | |
| *A61K 47/48* | (2006.01) | |
| *A61K 45/06* | (2006.01) | |
| *A61K 31/395* | (2006.01) | |
| *A61K 31/559* | (2006.01) | |
| *G01N 33/574* | (2006.01) | |

(52) U.S. Cl.
CPC ......... *A61K 47/48561* (2013.01); *A61K 31/395* (2013.01); *A61K 31/559* (2013.01); *A61K 45/06* (2013.01); *A61K 47/4863* (2013.01); *A61K 47/48384* (2013.01); *A61K 47/48569* (2013.01); *A61K 47/48607* (2013.01); *A61K 47/48715* (2013.01); *G01N 33/57484* (2013.01); *G01N 2333/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 6,441,163 B1 | 8/2002 | Chari et al. | |
| 7,276,497 B2 | 10/2007 | Chari et al. | |
| 7,301,019 B2 | 11/2007 | Widdison et al. | |
| 7,368,565 B2 | 5/2008 | Chari et al. | |
| 7,411,063 B2 | 8/2008 | Widdison et al. | |
| 7,432,088 B2 | 10/2008 | Kuo et al. | |
| 7,598,375 B2 | 10/2009 | Ho et al. | |
| 7,811,572 B2 | 10/2010 | Dai et al. | |
| 8,043,618 B2 | 10/2011 | Sun et al. | |
| 8,163,888 B2 | 4/2012 | Steeves et al. | |
| 8,383,122 B2 | 2/2013 | Dai et al. | |
| 2010/0098696 A1 | 4/2010 | Sun et al. | |
| 2011/0003969 A1 | 1/2011 | Kellogg et al. | |
| 2011/0166319 A1 | 7/2011 | Dai et al. | |
| 2012/0253021 A1 | 10/2012 | Li et al. | |
| 2012/0259100 A1 | 10/2012 | Jin | |

FOREIGN PATENT DOCUMENTS

| | | | |
|---|---|---|---|
| WO | 2013/083817 | * | 6/2013 |
| WO | 2014/055842 | * | 4/2014 |
| WO | 2014/160160 | * | 10/2014 |
| WO | 2014/163714 | * | 10/2014 |

OTHER PUBLICATIONS

Elkins, et al., FcRL5 as a target of antibody-drug conjugates for the treatment of multiple myeloma, Mol Cancer Ther 11(10):2222-2232 (2012).
Abhinandan, K.R., et al, Analysis and improvements to Kabat and structurally correct numbering of antibody variable domains, Molecular Immunology 45:3832-3839 (2008).
Burdon et al. eds., Laboratory Techniques in Biochemistry and Molecular Biology, vol. 13 (Elsevier Science Publishers, Amsterdam) in Monoclonal Antibody Technology, The Production and Characterization of Rodent and Human Hybridomas (Campbell ed., 1984).
Chothia, et al., Canonical Structures for the Hypervariable Regions of Immunoglobulins, J Mol Biol. 196:901-917 (1987).
Chothia, et al., Conformations of immunoglobulin hypervariable regions, Nature 342:877-883 (1989).
Coligan, et al., Current Protocols in Immunology, Wiley & Sons, Incorporated (2007).
Gennaro, et al., 19th ed. Remington: Practice of; The Science and Pharmacy, Mack Publishing Co. (1995).
Huse, et al., Generation of a Large Combinatorial Library of the Immunoglobulin Repertoire in Phage Lambda, Science 246:1275-1281 (1989).
Kabat, et al., Sequences of Proteins of Immunological Interest, Fifth ed, U.S. Department of Health and Human Services, NIH Publication No. 91-3242 (1991).
Kohler, et al., Continuous cultures of fused cells secreting antibody of predefined specificity, Nature 256:495-497 (1975).

(Continued)

*Primary Examiner* — Sheela J Huff
(74) *Attorney, Agent, or Firm* — Nicole S. Woods

(57) ABSTRACT

The invention provides conjugates that consist of a drug moiety agent and a cell binding agent that target human fibroblast growth factor receptor 3 (FGFR3). These conjugates have therapeutic use as they are designed and tailored to target a specific cell population and deliver a powerful cytotoxin inside the cell. The conjugate of the present invention has significant advantages over other conjugates known in the art by providing a targeted tumor therapy as well as bystander activity to neighboring cells in an important oncology receptor that is only moderately expressed.

18 Claims, No Drawings

(56) References Cited

OTHER PUBLICATIONS

Lohrisch, et al., An Overview of HER2, Seminars in Oncology, 28(6), Suppl 18:3-11 (2001).

Ritter, Antibody-Drug Conjugates; Looking Ahead to an Emerging Class of Biotherapeutic, Pharmaceutical Technology; PharmTech.com, p. 42-47 (2012).

Sambrook, et al., Molecular Cloning: A Laboratory Manual, 2nd ed., Cold Spring Harbor Laboratory Press (1989).

Oxford Molecular's AbM antibody modelling software, available at http://www.bioinf.org.uk/abs/.

* cited by examiner

SEQUENCE LISTING

<160> NUMBER OF SEQ ID NOS: 13

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Tyr Met Phe Thr Ser Tyr Gly Ile Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Trp Val Ser Thr Tyr Asn Gly Asp Thr Asn Tyr Ala Gln Lys Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Val Leu Gly Tyr Tyr Asp Ser Ile Asp Gly Tyr Tyr Gly Met Asp
1               5                   10                  15

Val

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Gly Gly Asn Asn Ile Gly Asp Lys Ser Val His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic

<400> SEQUENCE: 5

Leu Asp Thr Glu Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Gln Val Trp Asp Ser Gly Ser Asp His Val Val
1               5                   10

<210> SEQ ID NO 7
<211> LENGTH: 126
<212> TYPE: PRT
<213> ORGANISM: Artificial Sequence
<220> FEATURE:
<223> OTHER INFORMATION: Synthetic

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Thr Tyr Asn Gly Asp Thr Asn Tyr Ala Gln Lys Phe
    50                  55                  60

Gln Gly Arg Val Thr Val Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Val Leu Gly Tyr Tyr Asp Ser Ile Asp Gly Tyr Tyr Tyr Gly
            100                 105                 110

Met Asp Val Trp Gly Gln Gly Thr Thr Val Thr Val Ser Ser
        115                 120                 125

```
<210> SEQ ID NO 8
<211> LENGTH: 109
<212> TYPE: PRT
<213> ORGANISM: Artificial Sequence
<220> FEATURE:
<223> OTHER INFORMATION: Synthetic

<400> SEQUENCE: 8

Gln Ser Val Leu Thr Gln Pro Pro Ser Leu Ser Val Ala Pro Gly Lys
1               5                   10                  15

Thr Ala Thr Phe Thr Cys Gly Gly Asn Asn Ile Gly Asp Lys Ser Val
            20                  25                  30

His Trp Tyr Arg Gln Lys Pro Gly Gln Ala Pro Val Leu Val Met Tyr
        35                  40                  45

Leu Asp Thr Glu Arg Pro Ser Gly Ile Pro Glu Arg Met Ser Gly Ser
    50                  55                  60

Asn Phe Gly Asn Thr Ala Thr Leu Thr Ile Thr Arg Val Glu Ala Gly
65                  70                  75                  80

Asp Glu Ala Asp Tyr Tyr Cys Gln Val Trp Asp Ser Gly Ser Asp His
                85                  90                  95

Val Val Phe Gly Gly Gly Thr Lys Leu Thr Val Leu Gly
            100                 105

<210> SEQ ID NO 9
<211> LENGTH: 456
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Thr Ser Tyr
            20                  25                  30

Gly Ile Ser Trp Val Arg Gln Ala Pro Gly Gln Gly Leu Glu Trp Met
        35                  40                  45

Gly Trp Val Ser Thr Tyr Asn Gly Asp Thr Asn Tyr Ala Gln Lys Phe
    50                  55                  60

Gln Gly Arg Val Thr Val Thr Thr Asp Thr Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Arg Val Leu Gly Tyr Tyr Asp Ser Ile Asp Gly Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205
```

Cys Asn Val Asn His Lys Pro Ser Asn Thr Lys Val Asp Lys Arg Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 10
<211> LENGTH: 214
<212> TYPE: PRT
<213> ORGANISM: Artificial Sequence
<220> FEATURE:
<223> OTHER INFORMATION: Synthetic

<400> SEQUENCE: 10

Gln Ser Val Leu Thr Gln Pro Pro Ser Leu Ser Val Ala Pro Gly Lys
1               5                   10                  15

Thr Ala Thr Phe Thr Cys Gly Gly Asn Asn Ile Gly Asp Lys Ser Val
            20                  25                  30

His Trp Tyr Arg Gln Lys Pro Gly Gln Ala Pro Val Leu Val Met Tyr
        35                  40                  45

Leu Asp Thr Glu Arg Pro Ser Gly Ile Pro Glu Arg Met Ser Gly Ser
    50                  55                  60

Asn Phe Gly Asn Thr Ala Thr Leu Thr Ile Thr Arg Val Glu Ala Gly
65                  70                  75                  80

Asp Glu Ala Asp Tyr Tyr Cys Gln Val Trp Asp Ser Gly Ser Asp His
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Ala Glu Cys Ser
    210

<210> SEQ ID NO 11
<211> LENGTH: 795
<212> TYPE: PRT
<213> ORGANISM: Homo sapiens

<400> SEQUENCE: 11

Met Gly Ala Pro Ala Cys Ala Leu Ala Leu Cys Val Ala Val Ala Ile
1               5                   10                  15

Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Glu Leu Val
        35                  40                  45

Phe Gly Ser Gly Asp Ala Val Glu Leu Ser Cys Pro Pro Pro Gly Gly
    50                  55                  60

Gly Pro Met Gly Pro Thr Val Trp Val Lys Asp Gly Thr Gly Leu Val
65                  70                  75                  80

Pro Ser Glu Arg Val Leu Val Gly Pro Gln Arg Leu Val Leu Asn Ala
                85                  90                  95

Ser His Glu Asp Ser Gly Ala Tyr Ser Cys Arg Gln Arg Leu Thr Arg
            100                 105                 110

Val Leu Cys His Phe Ser Val Arg Val Thr Asp Ala Pro Ser Ser Gly
        115                 120                 125

Asp Asp Glu Asp Gly Glu Asp Glu Ala Glu Asp Thr Gly Val Asp Thr
    130                 135                 140

Gly Ala Pro Tyr Trp Thr Arg Pro Glu Arg Met Asp Lys Lys Leu Leu
145                 150                 155                 160

Ala Val Pro Ala Ala Asn Thr Val Arg Phe Arg Cys Pro Ala Ala Gly
                165                 170                 175

Asn Pro Thr Pro Ser Ile Ser Trp Leu Lys Asn Gly Arg Glu Phe Arg
            180                 185                 190

Gly Glu His Arg Ile Gly Gly Ile Lys Leu Arg His Gln Gln Trp Ser
        195                 200                 205

Leu Val Met Glu Ser Val Val Pro Ser Asp Arg Gly Asn Tyr Thr Cys
    210                 215                 220

Val Val Glu Asn Lys Phe Gly Ser Ile Arg Gln Thr Tyr Thr Leu Asp
225                 230                 235                 240

Val Leu Glu Arg Ser Pro His Arg Pro Ile Leu Gln Ala Gly Leu Pro
                245                 250                 255

Ala Asn Gln Thr Ala Val Leu Gly Ser Asp Val Glu Phe His Cys Lys

```
                260             265             270
Val Tyr Ser Asp Ala Pro His Ile Gln Trp Leu Lys His Val Glu Val
            275                 280             285

Asn Gly Ser Lys Val Gly Pro Asp Gly Thr Pro Tyr Val Thr Val Leu
290             295                 300

Lys Thr Ala Gly Ala Asn Thr Thr Asp Lys Glu Leu Glu Val Leu Ser
305             310              315                 320

Leu His Asn Val Thr Phe Glu Asp Ala Gly Glu Tyr Thr Cys Leu Ala
                325             330             335

Gly Asn Ser Ile Gly Phe Ser His His Ser Ala Trp Leu Val Val Leu
            340             345             350

Pro Ala Glu Glu Leu Val Glu Ala Asp Glu Ala Gly Ser Val Tyr
        355             360             365

Ala Gly Ile Leu Ser Tyr Gly Val Gly Phe Phe Leu Phe Ile Leu Val
        370             375             380

Val Ala Ala Val Thr Leu Cys Arg Leu Arg Ser Pro Lys Lys Gly
385             390             395             400

Leu Gly Ser Pro Thr Val His Lys Ile Ser Arg Phe Pro Leu Lys Arg
            405             410             415

Gln Val Ser Leu Glu Ser Asn Ala Ser Asn Ser Ser Asn Thr Pro Leu
            420             425             430

Val Arg Ile Ala Arg Leu Ser Ser Gly Glu Gly Pro Thr Leu Ala Asn
            435             440             445

Val Ser Glu Leu Glu Leu Pro Ala Asp Pro Lys Trp Glu Leu Ser Arg
        450             455             460

Ala Arg Leu Thr Leu Gly Lys Pro Leu Gly Glu Gly Cys Phe Gly Gln
465             470             475             480

Val Val Met Ala Glu Ala Ile Gly Ile Asp Lys Asp Arg Ala Ala Lys
                485             490             495

Pro Val Thr Val Ala Val Lys Met Leu Lys Asp Asp Ala Thr Asp Lys
            500             505             510

Asp Leu Ser Asp Leu Val Ser Glu Met Glu Met Met Lys Met Ile Gly
            515             520             525

Lys His Lys Asn Ile Ile Asn Leu Leu Gly Ala Cys Thr Gln Gly Gly
        530             535             540

Pro Leu Tyr Val Leu Val Glu Tyr Ala Ala Lys Gly Asn Leu Arg Glu
545             550             555             560

Phe Leu Arg Ala Arg Arg Pro Pro Gly Leu Asp Tyr Ser Phe Asp Thr
                565             570             575

Cys Lys Pro Pro Glu Glu Gln Leu Thr Phe Lys Asp Leu Val Ser Cys
            580             585             590

Ala Tyr Gln Val Ala Arg Gly Met Glu Tyr Leu Ala Ser Lys Cys Ile
            595             600             605

His Arg Asp Leu Ala Ala Arg Asn Val Leu Val Thr Glu Asp Asn Val
            610             615             620

Met Lys Ile Ala Asp Phe Gly Leu Ala Arg Asp Val His Asn Leu Asp
625             630             635             640

Tyr Tyr Lys Lys Thr Thr Asn Gly Arg Leu Pro Val Lys Trp Met Ala
                645             650             655

Pro Glu Ala Leu Phe Asp Arg Val Tyr Thr His Ser Asp Val Ser Phe
            660             665             670

Gly Val Leu Leu Trp Glu Ile Phe Thr Leu Gly Gly Ser Pro Tyr Pro
            675             680             685
```

| | | | | | | | | | | | |
|---|---|---|---|---|---|---|---|---|---|---|---|
|Gly|Ile|Pro|Val|Glu|Glu|Leu|Phe|Lys|Leu|Leu|Lys|Glu|Gly|His|Arg|
| |690| | | |695| | | |700| | | | | | |

| | | | | | | | | | | | |
|---|---|---|---|---|---|---|---|---|---|---|---|
|Met|Asp|Lys|Pro|Ala|Asn|Cys|Thr|His|Asp|Leu|Tyr|Met|Ile|Met|Arg|
|705| | | | |710| | | |715| | | | | |720|

| | | | | | | | | | | | |
|---|---|---|---|---|---|---|---|---|---|---|---|
|Glu|Cys|Trp|His|Ala|Ala|Pro|Ser|Arg|Pro|Thr|Phe|Lys|Leu|Val|Glu|
| | | |725| | | | |730| | | | |735| | |

```
Gly Ile Pro Val Glu Glu Leu Phe Lys Leu Leu Lys Glu Gly His Arg
    690             695             700

Met Asp Lys Pro Ala Asn Cys Thr His Asp Leu Tyr Met Ile Met Arg
705             710             715                     720

Glu Cys Trp His Ala Ala Pro Ser Arg Pro Thr Phe Lys Leu Val Glu
            725             730             735

Asp Leu Asp Arg Val Leu Thr Val Thr Ser Thr Asp Glu Tyr Leu Asp
            740             745             750

Leu Ser Ala Pro Phe Glu Tyr Ser Pro Gly Gly Gln Asp Thr Pro Ser
        755             760             765

Ser Ser Ser Ser Gly Asp Asp Ser Val Phe Ala His Asp Leu Leu Pro
    770             775             780

Pro Ala Pro Pro Ser Ser Gly Gly Ser Arg Thr
785             790             795
```

<210> SEQ ID NO 12
<211> LENGTH: 1368
<212> TYPE: DNA
<213> ORGANISM: Artificial Sequence
<220> FEATURE:
<223> OTHER INFORMATION: Synthetic

<400> SEQUENCE: 12

```
gaggtccagc tggtacagtc tggagctgag gtgaagaagc tggggcctc  agtgaaagtc      60
tcctgcaagg cttctggcta catgtttacc agctatggga tcagttgggt gcgacaggcc     120
cctggacaag gcttgagtg gatgggatgg gtcagcactt acaatggtga cacaaactat     180
gcgcagaagt tccagggcag agtcaccgtg accacagaca tccacgag  acagcctac      240
atggagctga ggagcctgag atctgaggac acggccgtgt attactgtgc gagagtcttg     300
ggatactatg atagtataga tggctactac tacggtatgg acgtctgggg ccaagggacc     360
acggtcaccg tctcaagcgc tagcaccaag ggcccatcgg tcttcccct ggcaccctcc      420
tccaagagca cctctggggg cacagcggcc ctgggctgcc tggtcaagga ctacttcccc     480
gaaccggtga cggtgtcgtg aactcaggc gccctgacca cggcgtgca ccttcccg        540
gctgtcctac agtcctcagg actctactcc ctcagcagcg tggtgaccgt gcctccagc     600
agcttgggca cccagaccta catctgcaac gtgaatcaca agcccagcaa caccaaggtg     660
gacaagagag ttgagcccaa atcttgtgac aaaactcaca catgcccacc gtgcccagca     720
cctgaactcc tggggggacc gtcagtcttc ctcttccccc caaaacccaa ggacaccctc     780
atgatctccc ggacccctga ggtcacatgc gtggtggtgg acgtgagcca cgaagaccct     840
gaggtcaagt tcaactggta tgtggacggc gtggaggtgc ataatgccaa gacaaagccg     900
cgggaggagc agtacaacag cacgtaccgt gtggtcagcg tcctcaccgt cctgcaccaa     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggaggagat gaccaagaac caagtcagcc tgacctgcct ggtcaaaggc    1140
ttctatccca gcgacatcgc cgtggagtgg gagagcaatg ggcagccgga gaacaactac    1200
aagaccacgc ctcccgtgct ggactccgac ggctccttct tcctctattc caagctcacc    1260
gtggacaaga gcaggtggca gcaggggaac gtcttctcat gctccgtgat gcatgaggct    1320
ctgcacaacc actacacgca gaagagcctc tccctgtctc cgggcaaa               1368
```

```
<210> SEQ ID NO 13
<211> LENGTH: 642
<212> TYPE: DNA
<213> ORGANISM: Artificial Sequence
<220> FEATURE:
<223> OTHER INFORMATION: Synthetic

<400> SEQUENCE: 13
cagtctgtgc tgactcagcc accctcactg tcagtggccc caggaaagac ggccaccttt      60
acctgtgggg gaaacaacat tggagacaag agtgttcact ggtaccggca gaagccaggc     120
caggcccctg tcctggtcat gtatcttgat accgaacggc cctcagggat ccctgagcga     180
atgtctggct ccaactttgg gaacacggcc accctgacga tcaccagggt cgaagccggg     240
gatgaggccg actattactg tcaggtgtgg gatagtggta gtgatcatgt ggtcttcggc     300
ggagggacca agctgaccgt cctaggtcag cctaaggctg ccccctcggt cactctgttc     360
ccgccctcct ctgaggagct tcaagccaac aaggccacac tggtgtgtct cataagtgac     420
ttctacccgg gagccgtgac agtggcctgg aaggcagata gcagccccgt caaggcggga     480
gtggagacca ccacaccctc aaacaaagc aacaacaagt acgcggccag cagctacctg      540
agcctgacgc ctgagcagtg gaagtcccac agaagctaca gctgccaggt cacgcatgaa     600
gggagcaccg tggagaagac agtggcccct gcagaatgct ct                         642
```

COMPOUNDS TO FIBROBLAST GROWTH FACTOR RECEPTOR-3 (FGFR3) AND METHODS OF TREATMENT

This application claims the benefit of U.S. Provisional Application No. 61/917,457 which was filed 18 Dec. 2013 and U.S. Provisional Application No. 61/928,025 which was filed 16 Jan. 2014.

This invention is directed to the fields of immunology, cancer treatment and targeted therapeutics. More specifically, the present invention is directed to a compound that is a conjugate of a toxic drug moiety, specifically a cytotoxic agent, and a cell binding agent, more specifically an antibody, and even more specifically an antibody that targets human fibroblast growth factor receptor 3 (FGFR3), via a linker moiety.

Delivering targeted toxic agents directly to aberrant cells rather than systematically treating the entire body as is done with traditional chemotherapy is the key advantage to targeted therapeutics. Targeted delivery helps minimize side effects by reducing damage to healthy cells. Conjugates of the invention are designed and tailored to target a specific cell population and deliver a powerful cytotoxin inside the cell while minimizing off-target cytotoxic activity. The present invention provides novel and useful conjugates and methods of treatment therewith, for elimination or reduced viability of abnormal cells while minimizing the effects on healthy cells.

The present invention is a response to a clinically unmet need for the treatment of bladder cancer, including transitional cell carcinoma (TCC), which is non-muscle invasive and mainly a local disease, and muscle invasive, which has a very high potential of being metastatic, hereinafter "M+", and multiple myeloma (MM). Cancer of the bladder will be newly diagnosed in an estimated 73,510 individuals and will cause 14,880 cancer related deaths in 2013 in the United States. This makes it the fourth most common neoplastic event in men and the ninth most common in women. About 70% of all new cases are TCC, non-muscle invasive cancer, with significant episodic recurrence for which a high unmet medical need exists to improve the current standard of care, which is bacillus Calmette-Guérin (BCG)/irradiation/surgery. Currently, there is no targeted therapy for muscle invasive bladder cancer, where the standard of care is a combination of four cytotoxic regimens of chemotherapy (methotrexate, vinblastine, doxorubicin, and cisplatin (MVAC)) that is frequently toxic. Accordingly, most patients are currently treated with the less optimal combination of gemcitabine and cisplatin. Multiple myeloma remains an incurable disease with overall survival currently ranging from three to five years. Currently, the standard of care for multiple myeloma is variable dosing of corticosteroids (dexamethasone) combined with cytotoxic regimens of chemotherapy, including vincristine, cyclophosphamide and doxorubicin, all drugs that have shown to be toxic to most patients.

There is a critical need for cancer treatments that effectively target a specific cell population and deliver a powerful cytotoxin while mitigating damage to healthy cells and tissue. Accordingly, the present invention provides a compound of the Formula I or a pharmaceutically acceptable salt thereof:

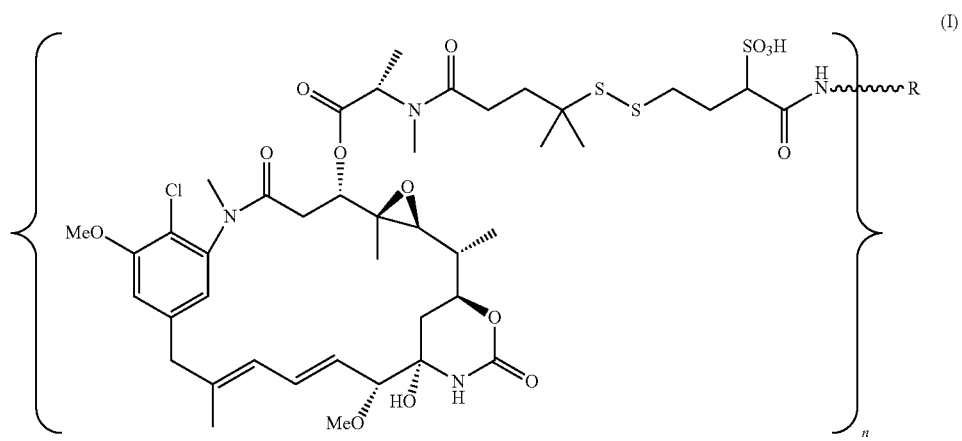

(I)

wherein n is an integer from 1-10 and
R is a cell binding agent that binds to human FGFR3 (SEQ ID NO 11) and comprises a CDRH1 having the sequence GYM-FTSYGIS (SEQ ID NO 1), a CDRH2 having the sequence WVSTYNGDTNYAQKFQG (SEQ ID NO 2), a CDRH3 having the sequence VLGYYDSIDGYYYGMDV (SEQ ID NO 3), a CDRL1 having the sequence GGNNIGDKSVH (SEQ ID NO 4), a CDRL2 having the sequence LDTERPS (SEQ ID NO 5), and a CDRL3 having the sequence QVWDSGSDHVV (SEQ ID NO 6). The present invention is hereinafter referred to as "Conjugate 1."

Scientific evidence herein suggests that the compound of the present invention is superior to the current standard of care for bladder cancer (muscle invasive and non-muscle invasive) and multiple myeloma in that it directly targets the aberrant cells and thereby reduces damage to healthy cells of the body, which in turn minimizes side effects. Additionally, the compound of the present invention is superior to other conjugates because it targets indications and patient populations where there is clinically unmet need. Unlike the currently approved conjugate Kadcyla®, the compound of the present invention capitalizes on a target which is pivotal in cancer formation yet would generally be considered inadequately over-expressed to be eligible for a conjugated target therapy. Unlike the currently approved conjugate Adcetris®, the compound of the present invention minimizes off-target toxicities thereby reducing adverse effects which are a known limitation of Adcetris®. Finally, unlike earlier approved conjugates such as gemutuzumab ozogamicin (Mylotarg®—approved by the FDA in 2000 but voluntarily withdrawn in 2010) which suffered from linker instability while in circulation, the compound of the present invention has a stable linker which thereby avoids instability in circulation.

Designing and engineering a conjugate is a complicated endeavor. It is far more complicated than merely selecting an antigen, a drug moiety, a linker moiety and a cell binding agent. (Ritter, A., Antibody-Drug Conjugates; Looking Ahead to an Emerging Class of Biotherapeutic, *Pharmaceutical Technology* pp 42-47 (January 2012)). The tumor antigen, the binding specificity of the cell binding agent, the mechanism of action of the drug moiety, and the manner in which the drug moiety is linked to the cell binding agent are all key determinants that govern the clinical activity and tolerability of the compound.

The conjugate of the present invention is a novel and inventive compound, not a combination of components. Engineering of the compound requires identification and selection of constituent functional groups (drug moiety, linker moiety, cell-binding agent) that complement one another. Each component is a functional group that has its own characteristics, benefits and constraints. The process is similar to the design of a novel small molecule comprised of distinct functional groups including but not limited to alkyl groups, carbonyl group, etc. Careful design to ensure balanced characteristics, benefits and constraints is required for the conjugate to be an effective therapeutic agent; however, the results are unpredictable. Selection of functional groups from the vast universe of drug moieties, linkers and cell binding agents is complicated and unpredictable. Although the functional groups may be previously disclosed (toxin: DM4 (N2'-deacetyl-N-2'(4-methyl-4-mercapto-1-oxopentyl)-maytansine) (U.S. Pat. No. 7,276,497), linker: sulfo-SPDB (N-succinimidyl 4-(2-pyridyldithio)-2-sulfobutanoate)) (U.S. Pat. No. 8,236,319), and cell binding agent: Antibody 1 (U.S. Pat. No. 8,043,618)), as with the structural activity relationships and chemical activities of small molecule compounds, for example methotrexate, vinblastine, doxorubicin, and cisplatin, knowledge of the individual functional groups does not impart knowledge of the functionality of the final compound.

The selection of a suitable target antigen is a key aspect of the present invention. The target antigen of the invention is FGFR3. Aberrant receptor tyrosine kinase (RTK) signaling plays a pivotal role in cancer formation as well as cancer progression. Fibroblast growth factors (FGFs) and their cognate receptors (FGFRs) are a part of the RTK family. FGFs and FGFRs play critical roles during embryonic development, tissue homeostasis and metabolism. Aberrant activation of FGFR3, through mutation, the generation of chromosomal fusions, or overexpression, has been directly linked to cancer with activated FGFR3 overexpression sufficient to induce oncogenic transformation.

Despite the prominence FGFR3 signaling pathways play in the treatment of cancer, FGFR3 is an unlikely antigen selection for the development of a conjugate therapy. For a conjugate to be effective, robust target expression on the tumor cell is commonly considered an essential requirement. Although FGFR3 is antigen positive, its over-expression on tumor cells versus normal cells is moderate; it is not expressed at an antigen level understood in the art to be necessary for and considered advantageous for typical conjugates, including those currently approved by the FDA. Given the modest expression levels of FGFR3, Conjugate 1 is unexpectedly efficacious. Activating mutations and fusions of FGFR3 have also been identified that further elicit unexpected efficaciousness of Conjugate 1.

Accordingly, engineering Conjugate 1 to include Antibody 1 as the cell binding agent is key aspect of the present invention. As the cell binding agent of Conjugate 1, Antibody 1 binds to the receptor and induces internalization and degradation of the receptor. Classical thought is that rapid replenishment of the surface antigen is required to enhance the likelihood of success of a therapeutic agent. Despite this, Conjugate 1 has been found to be particularly efficacious.

The selection of sulfo-SPDB as the linker is also a key aspect of the invention. Sulfo-SPDB was selected to balance the toxicity of the drug moiety by ensuring intracellular metabolism of the drug moiety inside the cell. However, sulfo-SPDB conjugates, when metabolized intracellularly, generate three metabolic products (lysine-N(epsilon)-sulfo-SPDB-DM4, DM4, and S-methyl-DM4), two of which are capable of promoting by-stander cell killing of neighboring cells through the delivery of free drug (DM4 and S-methyl-DM4), which can also increase toxicity through non-specific killing of normal cells. Due to the expression rates of the antigen, this effect was balanced, thereby turning a perceived disadvantage into an advantage of the conjugate of the present invention. Further, sulfo-SPDB was selected over other cleavable linkers, such as SPDB and SMCC, due to its superior efficacy in some tumor models as well as toxicity considerations.

Despite significant engineering and conjugation challenges, the conjugate of the present invention surprisingly enables cancer treatments that effectively target a specific cell population and delivers a powerful cytotoxin while mitigating damage to healthy tissue in a moderately expressed antigen that plays a pivotal role in cancer progression.

One aspect of the invention is the aforementioned Conjugate 1. The invention also relates to a compound wherein the cell binding agent further comprises a variable heavy amino acid sequence of:

```
                                              (SEQ ID NO 7)
EVQLVQSGAEVKKPGASVKVSCKASGYMFTSYGISWVRQAPGQGLEWMG

WVSTYNGDTNYAQKFQGRVTVTTDTSTSTAYMELRSLRSEDTAVYYCAR

VLGYYDSIDGYYYGMDVWGQGTTVTVSS
``` and a variable light amino acid sequence of:

```
                                              (SEQ ID NO 8)
QSVLTQPPSLSVAPGKTATFTCGGNNIGDKSVHWYRQKPGQAPVLVMYL

DTERPSGIPERMSGSNFGNTATLTITRVEAGDEADYYCQVWDSGSDHVV

FGGGTKLTVLG.
```

The invention relates to a compound wherein the cell binding agent further comprises a light chain comprising the amino acid sequence of SEQ ID NO: 10 and a heavy chain comprising the amino acid sequence of SEQ ID NO: 9. The invention also relates to the compound wherein the cell binding agent further comprises two light chains each comprising the amino acid sequence of SEQ ID NO: 10 and two heavy chains each comprising the amino acid sequence of SEQ ID NO: 9.

In one aspect of the invention, the compounds have a drug-to-antibody ratio or as used herein "DAR", of 2.0 to 5.0. In another aspect of the invention, the compound has a DAR of 3.5±0.5.

The invention also relates to a pharmaceutical composition comprising the aforementioned compounds together with a pharmaceutically acceptable carrier, diluent or excipient. The pharmaceutical composition may further comprise an additional pharmaceutical agent.

One aspect of the invention is the compound for use in therapy. Another aspect is the compound for use in treating cancer.

In another aspect, the invention is the compound for use in treating cancer in a patient having a level of FGFR3 expression that is greater than the level of FGFR3 expression in a control population. In one aspect, the control population comprises at least one individual not suffering from cancer.

In another aspect, the invention is the compound for use in treating cancer in a patient, wherein the patient has an elevated level of FGFR3 expression and the treatment comprises determining whether or not the patient has an elevated level of FGFR3 expression by ex vivo or in vitro determining the level of FGFR3 expression in a biological sample of the patient and comparing the level of FGFR3 expression in said sample with the level of FGFR3 expression in a control sample.

In one aspect, the control sample is a biological sample from an individual not suffering from cancer.

In a further aspect, the biological sample of the patient is selected from the group consisting of blood, serum, plasma, urine and tissue. In a still further aspect, the control sample is from the same source as the biological sample of the patient. For instance, if the biological sample from the patient is a blood sample, the control sample is also a blood sample.

In another aspect, the invention is the compound for use in treating cancer in a patient having (a) a mutation of FGFR3 (SEQ ID NO 11), wherein the mutation is selected from the group consisting of S249C, R248C, Y373C, Y375C, and combinations thereof; (b) a fusion of FGFR3-TACC3; or (c) a combination of (a) and (b).

In another aspect, the invention is the compound for use in treating cancer in a patient having (a) a mutation of FGFR3 (SEQ ID NO 11), wherein the mutation is selected from the group consisting of S249C, R248C, Y373C, Y375C, and combinations thereof; (b) a fusion of FGFR3-TACC3; or (c) a combination of (a) and (b), and the treatment comprises determining whether or not the patient has (a) a mutation of FGFR3 (SEQ ID NO 11), wherein the mutation is selected from the group consisting of S249C, R248C, Y373C, Y375C, and combinations thereof; (b) a fusion of FGFR3-TACC3; or (c) a combination of (a) and (b), by ex vivo or in vitro determining the presence of (i) one or more of the S249C, R248C, Y373C, Y375C mutations; (ii) a fusion of FGFR3-TACC3; or (iii) a combination of (i) and (ii) in a biological sample of the patient.

In a further aspect, the biological sample of the patient is selected from the group consisting of blood, serum, plasma, urine, tissue, tumor cells, tumor tissue samples, circulating tumor cells, and circulating DNA.

In some aspects, the cancer is bladder cancer or multiple myeloma.

In another aspect, the compound may be administered simultaneously, separately or sequentially with another anticancer treatment. The anti-cancer treatment is selected from the group consisting of an anti-angiogenic agent, a chemotherapeutic agent, and an anti-neoplastic agent. In one aspect of the invention, the anti-neoplastic agent is cisplatin.

The invention also relates to a method of treating cancer in a mammal, comprising administering to said mammal in need thereof an effective amount of the compound wherein the cancer is selected from the group consisting of bladder or multiple myeloma. The method may further comprise administering another anti-cancer treatment to said mammal wherein said anti-cancer treatment is selected from the group consisting of an anti-angiogenic agent, a chemotherapeutic agent, and an anti-neoplastic agent. In one aspect, the anti-neoplastic agent is cisplatin.

One aspect of the invention is a method of treating cancer in a patient, comprising the steps: (1) measuring the expression level of FGFR3 (SEQ ID NO 11) in a sample taken from the patient, wherein the sample is selected from the group consisting of blood, serum, plasma, urine, and tissue, and (2) administering to the patient the compound if the FGFR3 expression level is above the FGFR3 expression level found in a control population.

One aspect of the invention is a method of treating cancer in a patient, comprising the steps: (1) determining the presence of an anomaly in a sample taken from the patient, wherein the anomaly is: (a) a mutation of FGFR3 (SEQ ID NO 11), wherein the mutation is selected from the group consisting of S249C, R248C, Y373C, Y375C, and combinations thereof, (b) a fusion of FGFR3-TACC3, or (c) a combination of (a) and (b), and wherein the sample is selected from the group consisting of blood, serum, plasma, urine, tissue, tumor cells, tumor tissue samples, circulating tumor cells, and circulating DNA, and (2) administering to the patient the compound if the anomaly is present.

One aspect of the invention is a method of treating cancer in a patient, comprising the steps: (1) determining the presence of a S249C mutation of FGFR3 (SEQ ID NO 11) in a sample taken from the patient wherein the sample is selected from the group consisting of blood, serum, plasma, urine, tissue, tumor cells, tumor tissue samples, circulating tumor cells, and circulating DNA, and (2) administering to the patient the compound if the S249C mutation is present.

One aspect of the invention is a method of treating cancer in a patient, comprising the steps: (1) determining the presence of a R248C mutation of FGFR3 (SEQ ID NO 11) in a sample taken from the patient wherein the sample is selected from the group consisting of blood, serum, plasma, urine, tissue, tumor cells, tumor tissue samples, circulating tumor cells, and circulating DNA, and (2) administering to the patient the compound if the R248C mutation is present.

Another aspect of the invention is a method of treating cancer in a patient, comprising the steps: (1) determining the presence of a Y373C mutation of FGFR3 (SEQ ID NO 11) in a sample taken from the patient wherein the sample is selected from the group consisting of blood, serum, plasma, urine, tissue, tumor cells, tumor tissue samples, circulating tumor cells, and circulating DNA, and (2) administering to the patient the compound if the Y373C mutation is present.

Another aspect of the invention is a method of treating cancer in a patient, comprising the steps: (1) determining the presence of a Y375C mutation of FGFR3 (SEQ ID NO 11) in a sample taken from the patient wherein the sample is selected from the group consisting of blood, serum, plasma, urine, tissue, tumor cells, tumor tissue samples, circulating tumor cells, and circulating DNA, and (2) administering to the patient the compound if the Y375C mutation is present.

Another aspect of the invention is a method of treating cancer in a patient, comprising the steps: (1) determining the presence of a fusion of FGFR3-TACC3 in a sample taken from the patient wherein the sample is selected from the group consisting of blood, serum, plasma, urine, tissue, tumor cells, tumor tissue samples, circulating tumor cells, and circulating DNA, and (2) administering to the patient the compound if the fusion of FGFR3-TACC3 is present.

One aspect of the invention is a method for determining whether a subject having a cancer is a candidate for the compound comprising ex vivo or in vitro determining the level of FGFR3 (SEQ ID NO 11) expression in a sample of the subject, wherein the sample is selected from the group consisting of blood, serum, plasma, urine, and tissue, wherein an increase in the level of FGFR3 expression as compared with the level of FGFR3 expression in an individual not suffering from cancer, is indicative that the subject is a candidate for the compound.

Another aspect is a method for determining whether a subject having a cancer is a candidate for the compound comprising ex vivo or in vitro determining the presence of an anomaly in a sample taken from a patient, wherein the anomaly is: (1) a mutation of FGFR3 (SEQ ID NO 11) wherein the mutation is selected from the group consisting of S249C, R248C, Y373C, Y375C, and combinations thereof, (2) a fusion of FGFR3-TACC3, or (3) a combination of (a) or (b), and wherein the sample is selected from the group consisting of blood, serum, plasma, urine, tissue, tumor cells, tumor tissue samples, circulating tumor cells, and circulating DNA, and wherein a detection of the mutation is indicative that the subject is a candidate for the compound.

One aspect of the invention is a method for determining whether a subject having a cancer is a candidate for the compound, comprising ex vivo or in vitro determining the presence of a S249C mutation of FGFR3 (SEQ ID NO 11) in a sample of the subject, wherein the sample is selected from the group consisting of blood, serum, plasma, urine, tissue, tumor cells, tumor tissue samples, circulating tumor cells, and circulating DNA, wherein a detection of the S249C mutation is indicative that the subject is a candidate for the compound.

One aspect of the invention is a method for determining whether a subject having a cancer is a candidate for the compound comprising ex vivo or in vitro determining the presence of a R248C mutation of FGFR3 (SEQ ID NO 11) in a sample of the subject, wherein the sample is selected from the group consisting of blood, serum, plasma, urine, tissue, tumor cells, tumor tissue samples, circulating tumor cells, and circulating DNA, wherein a detection of the R248C mutation is indicative that the subject is a candidate for the compound.

Another aspect is a method for determining whether a subject having a cancer is a candidate for the compound comprising ex vivo or in vitro determining the presence of a Y373C mutation of FGFR3 (SEQ ID NO 11) in a sample of the subject, wherein the sample is selected from the group consisting of blood, serum, plasma, urine, tissue, tumor cells, tumor tissue samples, circulating tumor cells, and circulating DNA, wherein a detection of the Y373C mutation is indicative that the subject is a candidate for the compound.

Another aspect is a method for determining whether a subject having a cancer is a candidate for the compound comprising ex vivo or in vitro determining the presence of a Y375C mutation of FGFR3 (SEQ ID NO 11) in a sample of the subject, wherein the sample is selected from the group consisting of blood, serum, plasma, urine, tissue, tumor cells, tumor tissue samples, circulating tumor cells, and circulating DNA, wherein a detection of the Y375C mutation is indicative that the subject is a candidate for the compound.

Another aspect is a method for determining whether a subject having a cancer is a candidate for the compound comprising ex vivo or in vitro determining the presence of a fusion of FGFR3-TACC3 in a sample of the subject, wherein the sample is selected from the group consisting of blood, serum, plasma, urine, tissue, tumor cells, tumor tissue samples, circulating tumor cells, and circulating DNA, wherein a detection of the fusion of FGFR3-TACC3 is indicative that the subject is a candidate for the compound.

As used herein, the term "antigen" includes a protein located on a cell's surface. Antigens can include polypeptides, carbohydrates, nucleic acids, lipids, haptens or other naturally occurring or synthetic compounds. Preferably, the antigen is a folded polypeptide or protein. Specific ligands bind the protein or receptor, initiating signal transduction and a change in cellular activity. Antibodies can also bind the antigen which can block ligand binding and the resulting signal transduction. The terms antigen, "receptor," "target" or "target antigen" are used interchangeably herein.

As used herein, the term "anomaly" includes any change in the sequence of the antigen that deviates from what is wild type, standard, normal or expected. Anomalies include genetic anomalies. Anomalies include mutations of all types and fusions.

As used herein, the term "mutation" includes changes in the nucleotide sequence of the genome including changes in the amino acid sequence of the antigen.

As used herein, the term "fusion" includes proteins created through the joining of two or more genes which originally coded for separate proteins. Fusion genes are commonly created when a chromosomal translocation replaces exons of one gene with intact exons from a second gene. This creates a single gene which can be transcribed, spliced, and translated to produce a functional fusion protein.

Overexpression of wild type FGFR3 is sufficient to induce oncogenic transformation. Aberrant activation resulting in constitutive, ligand independent activity of FGFR3 (SEQ ID NO: 11), through mutation, has been directly linked to cancer. Identified mutations include S249C, R248C, Y373C, and Y375C. Several fusion proteins that splice exons of the target FGFR3 with exons of the transforming acidic coil coil protein 3 (TACC3), as used herein as "FGFR3-TACC3 fusion" have been identified in numerous cancers. These mutations and some fusions as seen in Table 5 render FGFR3 hypersensitive and thus more receptive to the conjugate of the present invention.

As used herein, the term "overexpression" includes the excessive expression of a gene wherein the gene produces an elevated level of its product including one or more receptors, which is associated with increased receptor activation and signaling. A cancer which "overexpresses" an antigenic receptor is one which has significantly higher levels of the receptor at the cell surface as compared to noncancerous cells of the same tissue. Receptor overexpression may be determined in a diagnostic or prognostic assay by evaluating increased levels of the receptor protein present on the surface of the cell via an immunohistochemistry (IHC) assay, or measuring the levels of receptor-ending nucleic acid in the cell via fluorescent in situ hybridization (FISH), southern blotting, northern blotting, or polymerase chain reaction (PCR).

Overexpression is not a finite limit but rather a continuum. Receptor cell surface expression or relative receptor cell surface density can be measured by median fluorescence intensity (MFI). For example FGFR3 cell surface expression presents at 11,000 receptors in the bladder cancer cell line BFTC-905 (wild type) and 16,000 FGFR3 receptors in the RT112 bladder tumor cell line (wild type and FGFR3-TACC3 fusion receptors). (See Table 5.) Kadcyla®, also known as TDM1, one of two approved conjugates in the United States, targets HER-2 which averages 2 million receptors in metastatic breast tumors. (Lohrisch, et al., Seminars in Oncology, Vol 28, No 6, Suppl 18: 3-11 (2001)). Although FGFR3 can be overexpressed, the quantity of FGFR3 protein expression is moderate and the tumor-normal differential expression is not as significant when compared to the quantities of other cancer-related proteins such as HER-2, which are considered highly overexpressed.

The term "conjugate" as used herein refers to a drug moiety or a derivative thereof that is linked to a cell binding agent (e.g., an antibody or fragment thereof) and is defined by a generic formula: (D-L)$_n$-R, wherein D is drug moiety, L is linker, R is cell binding agent comprising antibody or antibody fragment and n is an integer which identifies the number of drug moieties and linkers attached to each cell binding agent. A conjugate is also known as an "immunoconjugate," an "antibody drug conjugate" or an "ADC".

The conjugate of the present invention is a monoclonal antibody-maytansinoid conjugate formed by covalent attachment of available lysine residues on the anti-FGFR3 antibody (Antibody 1), to cleavable linkers (sulfo-SPDB) with the active maytansinoid (DM4) attached to the linker via disulfide bonding.

Conjugates are compounds that are tailored to target a specific cell population and deliver a powerful cytotoxin inside the cell. A conjugate can be considered a prodrug in that when it is administered, it is essentially nontoxic until it is internalized into the abnormal cell.

The average loading for a sample of a conjugate is referred to herein as the DAR, maytansinoid-to-antibody ratio "MAR" or "drug load." DAR, as used herein, refers to the number of drug molecules (e.g., a maytansinoid) that are linked or attached to a cell binding agent (e.g., an anti-FGFR3 antibody). While the DAR has an exact value for a specific conjugate molecule (e.g., n in Formula (I)), it is understood that the value will often be an average value when used to describe a sample containing many molecules, due to the presence of different conjugate molecules having different drug to antibody ratios. In one aspect the number of drug molecules that can be attached to a cell binding agent can average from about 1 to about 10. In one aspect of the invention, the DAR averages 2 to 8. In other aspects of the invention, the DAR averages 2 to 5. In yet other aspect of the invention, the DAR averages 3 to 5. In yet other aspect of the invention, the DAR averages 3 to 4. In some aspects, a DAR of 'about n' means the measured value for DAR is within n±0.5. In one aspect of the invention, the DAR averages 3.5±0.5. The anti-tumor activity of the conjugate can be more efficacious as compared to a drug load of a lesser number of drugs linked to the same cell binding agent, while increasing the number of drugs linked can improve potency, but at the cost of altered pharmacokinetic properties for the cell binding agent. The method used for conjugation and the methodology and techniques to measure and calculate DAR may impact the DAR value of the compound.

Consistency and reproducibility of the DAR ensures delivery of a consistent dose and pharmacokinetics for a specified ADC. A low DAR can result in the development of a conjugate with lower cytotoxic activity. However, a high DAR can affect the affinity to the receptor, receptor binding and blocking activity as well as conjugate stability in vivo.

As used herein, the term "toxin" is any substance capable of having an adverse effect on the growth or proliferation of a cell, resulting in the death of a cell, inducing cell death, or in some manner decreasing cell viability. As used herein, the term "cytotoxin" or "cytotoxic agents" includes toxins that are activated in the cytoplasm.

As used herein, the terms "drug moiety," "drug" or "payload" includes toxins, cytotoxins or cytotoxic agents. One type of drug moiety includes the maytansine class of compounds.

As used herein, the term "maytansinoids," include cytotoxin microtubule-targeted compounds that inhibit proliferation of cells at mitosis. This includes N2'-deacetyl-N-2'(4-methyl-4-mercapto-1-oxopentyl)-maytansine, known as "DM4" (Formula II):

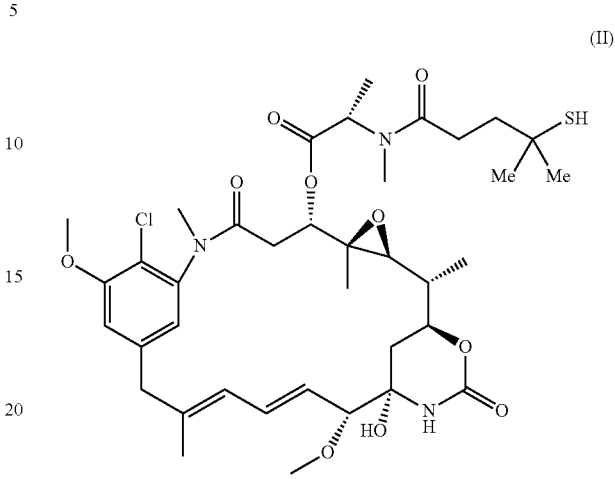

Maytansinoids are shown to be 100 to 1000 fold more cytotoxic than conventional cancer chemotherapeutic agents. Although highly efficacious, maytansinoids have proven to be too toxic when administered to patients systemically in Phase 1 trials. However, when administered as part of a targeted treatment such as a conjugate, the highly cytotoxic nature of maytansinoids is delivered directly to aberrant or damaged cells thus mitigating toxic, systemic effects on healthy cells in the body that do not express the target or antigen. The advantage is two-fold. First, greater cytotoxicity allows for more efficient cell death and decreased cell viability. Second, greater cytotoxicity may allow for a lower dosage to be administered with the same results to the cell. This provides a more potent therapeutic option for patients with a reduced adverse event spectrum.

As used herein, the term "linker moiety" or "linker" refers to a chemical moiety that acts as a binding agent that connects a cell binding agent to a drug moiety. More specifically, a linker moiety comprises a covalent bond or atoms that covalently bind a cell binding agent to a drug moiety. The linker can be any bridging compound that enables metabolic release of the payload within cancer cells and some promote subsequent metabolite-dependent bystander cell killing. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active.

The drug moiety, for example, is linked to the cell binding agent, in the present invention Antibody 1, the anti-FGFR3 antibody of the conjugate, through a disulfide bond. The linker molecule or crosslinking agent comprises a reactive chemical group that can react with lysine residues or other residues of the cell binding agent. The reactive chemical group for reaction with the cell-binding agent can be N-succinimidyl esters and N-sulfosuccinimidyl esters. Additionally the linker molecule comprises a reactive chemical group, which can be a dithiopyridyl group that can react with the drug moiety to form a disulfide bond.

For example, cell binding agent can be modified with crosslinking reagents and the cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

Sulfo-SPDB or sSPDB (which are used interchangeably herein), N-succinimidyl 4-(2-pyridyldithio)-2-sulfobutanoate, Formula III, is a cleavable linker that allows the conjugate to be cleaved inside the target cell in the cytosol due to the reducing intracellular environment. Formula III:

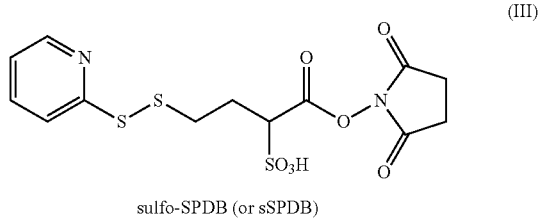 [SMILES: O=C(ON1C(=O)CCC1=O)C(CCSSc1ccccn1)S(=O)(=O)O]

sulfo-SPDB (or sSPDB)

As a cleavable linker, sulfo-SPDB permits enhanced bystander cell killing by the free drug given the metabolic processing of the conjugate to generate DM4, and S-methyl-DM4. In the present invention, the antibody of the conjugate connects to the linker via a free surface exposed lysine residue which in turn links to the cytotoxin of the conjugate via a thio group. When conjugated with a maytansinoid, the charged metabolite has decreased hydrophobicity, which decreases the activity of MDR efflux pumps and thus provides an opportunity for increased cell killing via decreased MDR-1 specific multidrug resistance.

As used herein, the expression "linked to a cell-binding agent" or "linked to an anti-FGFR3 antibody or fragment" refers to the conjugate molecule comprising at least one drug derivative bound to a cell binding agent, e.g. anti-FGFR3 antibody of Conjugate 1 via a suitable linking group, or a precursor thereof.

The metabolic pathways for conjugates vary, however, upon internalization by target cells. Maytansinoid conjugates undergo rapid degradation of the cell binding component in the low pH lysosome, resulting in the release of metabolic products from the maytansinoid drug that is attached via the linker to one amino acid (a lysine residue) of the cell binding agent. In the case of a disulfide linked conjugate, such as sulfo-SPDB-DM4, the maytansinoid-modified lysine residue undergoes disulfide reduction to release the thiol-containing drug, which can then undergo methylation, presumably catalyzed by an intracellular methyltransferase enzyme to give the highly potent S-methyl-maytansinoid (S-methyl-DM4) or can simply result in the production of non-modified maytansine (DM4). This released drug is able to diffuse out of the cell and reduce the viability of neighboring cells via what has been defined and described as a bystander effect. Given the observed target heterogeneity for most cell surface receptors, the 'bystander' phenomenon may be an important mechanism of in vivo cell killing because all cells in a tumor population may not express the antigen to the same degree.

As used herein, the term "antibody" includes immunoglobulin molecules comprising four polypeptide chains, two heavy (H) chains and two light (L) chains inter-connected by disulfide bonds. Individual chains can fold into domains having similar sizes (110-125 amino acids) and structures, but different functions. Antibody may be abbreviated herein as "Ab."

The light chain can comprise one variable domain (abbreviated herein as VL) and/or one constant domain (abbreviated herein as CL). The light chains of human antibodies (immunoglobulins) are either kappa (K) light chains or lambda (λ) light chains. The expression VL, as used herein, is intended to include both the variable regions from kappa-type light chains (VK) and from lambda-type light chains (Vλ). The heavy chain can also comprise one variable domain (abbreviated herein as VH) and/or, depending on the class or isotype of antibody, three or four constant domains (CH1, CH2, CH3 and CH4) (abbreviated herein collectively as CH). In humans, the isotypes are IgA, IgD, IgE, IgG, and IgM, with IgA and IgG further subdivided into subclasses or subtypes (IgA1-2 and IgG1-4). The present invention includes antibodies of any of the aforementioned classes or subclasses. Human IgG$_1$ is the preferred isotype for the antibodies of the conjugate of the present invention.

Three regions, called hypervariable or complementarity-determining regions (CDRs), are found in each of VL and VH, which are supported by less variable regions called frameworks (abbreviated herein as FR). Amino acids are assigned to a particular CDR region or domain in accordance with Kabat convention (Kabat, et al., Sequences of Proteins of Immunological Interest, Fifth Edition, U.S. Department of Health and Human Services, NIH Publication No. 91-3242 (1991)), Chothia convention (Chothia, et al., J Mol Biol. 1987; 196: 901-917. Chothia, et al., Nature. 1989; 342: 877-883), and/or Oxford Molecular's AbM antibody modelling software (Abhinandan, et al., Molecular Immunology. 2008; 45: 3832-3839). Each VH and VL is composed of three CDRs and four FRs, arranged from amino-terminus to carboxy-terminus in the following order: FR1-CDR1-FR2-CDR2-FR3-CDR3-FR4. The portion of an antibody consisting of VL and VH domains is designated Fv (Fragment variable) and constitutes the antigen-binding site. Single chain Fv (scFv) is an antibody fragment containing a VL domain and a VH domain on one polypeptide chain, wherein the N terminus of one domain and the C terminus of the other domain are joined by a flexible linker.

Antibody 1, the cell binding agent of the conjugate of the present invention is monoclonal antibody that has a lambda (λ) light chain. The antibody structure of Conjugate 1 contains the typical number of approximately 100 free lysine side residues in positions that permit conjugation with minimal steric hindrance. It is highly specific to both splice forms of FGFR3 (FGFR3(IIIb) and FGFR3(IIIc)) and is internalized upon binding to FGFR3. However, Antibody 1 has a slightly lower isoelectric point (pI) than most antibodies which can affect stability as well as the conjugation process. Additionally Antibody 1 induces receptor degradation upon binding to the FGFR3 receptor which is generally viewed as a disadvantage. With its lower pI and lambda light chain, Antibody 1 imparts unique challenges to the compound. Despite challenges with instability the conjugate has proven to be surprisingly efficacious.

The term "isolated" refers to an antibody, protein, peptide or nucleic acid which is free or substantially free from other macromolecular species found in a cellular environment. "Substantially free," as used herein means the protein peptide or nucleic acid of interest comprises more than 80% (on a molar basis) of the macromolecular species present, preferably more than 90% and more preferably more than 95%. Examples of "isolated" antibodies include an antibody that has been affinity purified, an antibody that has been made by a hybridoma or other cell line in vitro, and a human antibody derived from a transgenic mouse.

The term "naked antibody," as used herein, refers to unconjugated antibody material.

The term "monoclonal antibody," as used herein, refers to an antibody obtained from a population of substantially homogeneous antibodies, e.g., the individual antibodies comprising the population are substantially identical except for possible naturally occurring mutations or minor post-translational variations that may be present. Monoclonal antibodies are highly specific, being directed against a single antigenic site (also known as determinant or epitope). Furthermore, in contrast to conventional (polyclonal) antibody preparations which typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. Monoclonal antibody may be abbreviated herein as "mAb."

The term "human antibody," as used herein, includes antibodies having variable and constant regions corresponding to human germline immunoglobulin sequences (as described in Kabat et al., supra). The human antibodies of the conjugate of the present invention may include amino acid residues not encoded by human germline immunoglobulin sequences (e.g., mutations introduced by random or site-specific mutagenesis in vitro or by somatic mutation in vivo), for example in the CDRs. The human antibody can have at least one position replaced with an amino acid residue, e.g., an activity enhancing amino acid residue which is not encoded by the human germline immunoglobulin sequence. However, the term "human antibody," as used herein, is not intended to include antibodies in which CDR sequences derived from the germline of another mammalian species, such as a mouse, have been grafted onto human framework sequences. Methods of producing a "human antibody," as used herein are not intended to include antibodies produced in a human being.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences.

Thus, antibodies of the conjugate in the present invention include, but are not limited to, isolated antibodies, human antibodies, humanized antibodies, recombinant human antibodies, monoclonal antibodies, specified portions and variants thereof; each containing at least one CDR.

Specificity of antibodies or fragments thereof can be determined based on affinity. Affinity, represented by the equilibrium constant for the dissociation of an antigen with an antibody ($K_D$), measures the binding strength between an antigenic determinant and an antibody-binding site. Affinity can be measured for example by surface plasmon resonance.

The antibodies, or fragments thereof, of the invention bind to an epitope of FGFR3 located on the extracellular domain segments (hereinafter referred simply to as "domains" or "ECD"). The term "epitope" as used herein refers to discrete, three-dimensional sites on an antigen that are recognized by the antibodies of the invention.

In addition to the antibodies specifically described herein, other "substantially homologous" modified antibodies can be readily designed and manufactured utilizing various recombinant DNA techniques well known to those skilled in the art. For example, the framework regions can vary from the native sequences at the primary structure level by several amino acid substitutions, terminal and intermediate additions and deletions, and the like. Moreover, a variety of different human framework regions may be used singly or in combination as a basis for the humanized immunoglobulins included in the present invention. In general, modifications of the genes may be readily accomplished by a variety of well-known techniques, such as site-directed mutagenesis.

The present invention includes nucleic acid sequences that encode an anti-FGFR3 antibody component of the conjugate heavy chain, comprising any one of the VH regions or a portion thereof, or any one of the VH CDRs, including any variants thereof, as disclosed herein. The antibody component of the conjugate of the present invention includes antibodies comprising the same CDR regions of Antibody 1, and/or the same light chain variable region and/or heavy chain variable region of Antibody 1.

The antibodies of Conjugate 1 may be produced by methods known in the art. These methods include the immunological method described by Kohler and Milstein, Nature 256: 495-497 (1975); Laboratory Techniques in Biochemistry and Molecular Biology, Volume 13 (Burdon et al. eds., Elsevier Science Publishers, Amsterdam) in Monoclonal Antibody Technology, The Production and Characterization of Rodent and Human Hybridomas (Campbell ed., 1984); as well as by the recombinant DNA method described by Huse et al., Science 246: 1275-1281 (1989). The antibodies of Conjugate 1 can also be obtained from libraries bearing combinations of VH and VL domains in the form of scFv or antigen binding fragment (Fab). The VH and VL domains can be encoded by nucleotides that are synthetic, partially synthetic, or naturally derived. The present invention can be made by phage display libraries bearing human antibody fragments. Other sources of human antibodies are transgenic mice engineered to express human immunoglobulin genes.

It is understood that amino acid residues that are primary determinants of binding of single domain antibodies can be within Kabat, Chothia, AbM, or a combination thereof defined CDRs, but may include other residues as well, such as, for example, residues that would otherwise be buried in the VH-VL interface of a VH-VL heterodimer.

Preferred host cells for transformation of vectors and expression of the antibodies of Conjugate 1 are mammalian cells, e.g., NS0 cells (non-secreting (0) mouse myeloma cells), 293, SP20 and CHO cells and other cell lines of lymphoid origin such as lymphoma, myeloma, or hybridoma cells. Other eukaryotic hosts, such as yeasts, can be alternatively used.

The antibodies of may be isolated or purified by any method known in the art, including precipitation by ammonium sulfate or sodium sulfate followed by dialysis against saline, ion exchange chromatography, affinity or immunoaffinity chromatography, as well as gel filtration or zone electrophoresis. A preferred method of purification for the antibodies of Conjugate 1 is Protein-A affinity chromatography.

Maytansinoids can be synthesized by techniques including, but not limited to, those detailed in U.S. Pat. Nos. 7,432,088, 7,301,019, 7,598,375, RE39,151 and 7,411,063.

The conjugates of the present invention can be prepared by a variety of methods known in the art, such as those described in U.S. Pat. Nos. 7,811,572, 8,383,122, 6,441,163, 7,368,565, 7,811,572, 8,163,888, and US application publications 2011/0003969, 2011/0166319, 2012/0253021 and 2012/0259100.

An alternative way to prepare the conjugates of the present invention is to concentrate the antibody to 30 mg/mL and diafilter into reaction buffer (50 mM EPPS, 20 mM sodium chloride, 2 mM EDTA, pH 8.2) for 10 diavolumes, and further concentrate to 45 g/L. A 1.2 molar ratio of DM4 (12 mM) relative to sulfo-SPDB (10 mM) is reacted with a 4.68 molar ratio of sulfo-SPDB relative to antibody in 167 mM EPPS, 66.7 mM NaCl, 2 mM EDTA, pH 8.2 and 70.0% (v/v) DMA. The in-situ reaction is carried out for 10±4 hours at 20±3° C., then added to the antibody with DMA to achieve a final antibody concentration of 20 mg/mL in 50 mM EPPS, 20 mM NaCl, 2 mM EDTA, pH 8.2±0.2 and 5.0% DMA (v/v). The conjugation reaction is carried out at 20.0±3.0° C. for 16±8 hours. After reaction, the conjugation mixture is rapidly pH adjusted to 5.0 by addition of 6.5% (v/v) of 1M acetic acid. The pH adjusted mixture is concentrated to 20 mg/mL, and diafiltered against basal formulation buffer (10 mM Acetate, pH 5.0±0.1) for 16 diavolumes. The purified conjugate is formulated at 5.0 mg/mL in 10 mM Acetate, 9% (w/v) Sucrose, 0.01% (w/v) Polysorbate-20 (Tween-20), pH 5.0, using concentrated stock solutions of sucrose (45%, w/v) and polysorbate-20 (10%, w/v).

The number of maytansinoid molecules bound per antibody molecule can be determined by measuring spectrophotometrically the ratio of the absorbance at 252 nm and 280 nm. Mass spectrometry enables the reproducibility of the conjugation process to be monitored. The average number of maytansinoid molecules to antibody can be, for example, 1-10, 2-8, 2-5, 3-5, 3-4, or 3.5±0.5.

To produce a commercially viable conjugate product, the conjugation process and buffer exchange must be efficient. During the development of Conjugate 1, it was found that the compound had solubility challenges and tended to precipitate out of solution when commonly used conjugation buffers were utilized. Factors such as net surface charge and the isoelectric point (pI) (the point where the molecule is neutral or has no net charge), can alter the solubility of the molecule and can create a stability issue resulting in precipitation. Numerous attempts using a variety of methods resulted in conjugated material that included aggregates and precipitation. Tolerance levels of aggregation and precipitation depend on the use of the compound; tolerance levels are often lower for materials intended for clinical trials or commercial production. It is unknown which characteristic, or characteristics, of Conjugate 1 may have caused these issues. For Conjugate 1, conjugation at basic pH proved to be challenging due to the difference in ionic strength required to maintain solubility of the antibody and conjugate at the reaction pH and the formulation pH. Specifically, Antibody 1 precipitated in low ionic strength buffer at basic pH used for the reaction, while Conjugate 1 precipitated in high ionic strength buffer at acidic pH used for conjugate formulation. The conjugation buffer required sufficient ionic strength to allow buffer exchange of Antibody 1 into basic pH reaction buffer, but low enough to allow buffer exchange of Conjugate 1 into acidic pH formulation buffer. Alternatively, dilution of the reaction mixture may be used to reduce ionic strength to the required level. Eventually, after significant engineering, it was found that Conjugate 1 required a balance between pH and salt for the reaction to go to completion to generate a stable and active compound that does not precipitate out of solution nor require other less desirable additives or techniques to maintain solubility.

Conjugates comprised of the maytansine payload can be evaluated for their ability to suppress or kill proliferating cells via target mediated activity and/or nonspecifically in vitro. For example, cell lines such as NCI-H226, NCI-H292, and NCI-H322M, can easily be used for the assessment of non-targeted cytotoxicity of the conjugate. Cells to be evaluated can be exposed to the compounds for 4 to 5 days and the surviving fractions of cells measured in direct assays by known methods. $IC_{50}$ values can then be calculated from the results of the assays. The target mediated cytotoxic activity of Conjugate 1 can also be evaluated by using cell lines that express different levels of the FGFR3 antigen.

In some aspects, the conjugates are capable of reducing tumor volume as measured by % T/C as defined more fully below.

A method of treating tumor growth in a mammal by administering to the mammal an efficacious dose of a conjugate is also provided by the present invention. Suitable conditions for treatment according to the present invention involve tumor cells that preferentially express FGFR3. While not intended to be bound to any particular mechanism, the present methods provide for treatment of the growth of cancer cells including for example, those in which neoplastic growth, bone metastases, organ transplant rejection or an immune disorder such as an autoimmune disease which is driven by or involves the expression of FGFR3.

"Treatment" or "treat," in the context of the present invention, refers to therapeutic treatment including slowing, lessening or reversing the progress of the underlying condition or undesired physiological change associated with a disease or disorder, or ameliorating clinical symptoms of a condition. Beneficial or desired clinical results include, but are not limited to, alleviation of symptoms, diminishment of the extent of a disease or disorder, stabilization of a disease or disorder (i.e., where the disease or disorder does not worsen), delay or slowing of the progression of a disease or disorder, amelioration or palliation of the disease or disorder, and remission (whether partial or total) of the disease or disorder, whether detectable or undetectable. Treatment can also mean prolonging survival as compared to expected survival if not receiving treatment. Those in need of treatment include those already with the disease. In one aspect, the present invention can be used as a medicament.

In the methods of the present invention, a therapeutically effective amount of a conjugate of the invention is administered to a mammal or patient in need thereof. Additionally, the pharmaceutical compositions of the invention may include a therapeutically effective amount of a conjugate of the invention. A "therapeutically effective amount" or "effective dose" refers to an amount effective, at dosages and for periods of time necessary, to achieve the desired therapeutic result. A therapeutically effective amount of the conjugate may vary according to factors such as the disease state, age, sex, and weight of the individual, and the ability of the conjugate to elicit a desired response in the individual. Other factors include administration, target site, physiological state of the patient, whether the patient is human or an animal, and other medications administered. Although compounds of the invention are particularly useful for administration to humans, they can be administered to other mammals as well. The term mammal as used herein is intended to include, but is not limited to, humans, laboratory animals, domestic pets and farm animals. A therapeutically effective amount is also one in which any toxic or detrimental effects of the conjugate are outweighed by the therapeutically beneficial effects.

Dosage regimens may be adjusted to provide the optimum desired response (e.g., a therapeutic response). Treatment dosages may be titrated using routine methods known to those of skill in the art to optimize safety and efficacy. Dosing schedules, for intravenous (i.v.) or non-intravenous administration, localized or systemic, or combinations thereof, will typically range from a single bolus dosage or continuous infusion to multiple administrations per day (e.g., every 4-6 hours), or as indicated by the treating physician and the patient's condition. An exemplary, non-limiting range for a therapeutically effective amount of Conjugate 1 is 0.1-50 mg/kg, more preferably 3-35 mg/kg, and more preferably 5-20 mg/kg. Dosing amounts and frequencies will be determined by the physicians treating the patient and may include doses from less than 1 mg/kg to over 100 mg/kg given daily, three times per week, weekly, once every two weeks, or less often. It should be noted, however, that the present invention is not limited to any particular dose.

The conjugate can be administered in combination with one or more other anti-cancer treatment, including but not limited to, an anti-angiogenic agent, a chemotherapeutic agent, and an anti-neoplastic agent. Any suitable anti-cancer agent can be used, such as a chemotherapeutic agent, radiation, antibody or combinations thereof.

Anti-cancer agents include, but are not limited to, anti-neoplastic agents, antibodies, adjuvants, and prodrugs. The anti-neoplastic agents which are presently known in the art, or being evaluated, can be grouped into a variety of classes including, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, and anti-angiogenic agents. Examples of alkylating agents include, but are not limited to, cisplatin, cyclophosphamide, melphalan, and dacarbazine. Examples of anti-metabolites include, but are not limited to, doxorubicin, daunorubicin, paclitaxel, gemcitabine, ALIMTA® and topoisomerase inhibitors include irinotecan (CPT-11), aminocamptothecin, camptothecin, DX-8951f, topotecan (topoisomerase I), etoposide (VP-16), and teniposide (VM-26) (topoisomerase II). When the anti-neoplastic agent is radiation, the source of the radiation can be either external (external beam radiation therapy—EBRT) or internal (brachytherapy—BT) to the patient being treated. The dose of anti-neoplastic agent administered depends on numerous factors, including, for example, the type of agent, the type and severity tumor being treated, and the route of administration of the agent. It should be emphasized, however, that the present invention is not limited to any particular dose or dosing regimen. In one aspect, cisplatin is a preferred anti-neoplastic agent of the invention.

The conjugate of the invention could also be administered with antibodies and/or small molecule inhibitors that inhibit and/or modulate other cell surface receptors involved in tumor growth or angiogenesis. The conjugate can also be administered in combination with one or more suitable adjuvants, such as, for example, cytokines (IL-10, IL-4 and IL-13) or other immune modulators, such as, but not limited to, chemokine, tumor-associated antigens, and peptides.

In the present invention, any suitable method or route can be used to administer the conjugate of the invention, and optionally, to co-administer anti-neoplastic agents and/or antagonists of other receptors. In a combination therapy of the present invention, the conjugate can be administered simultaneously, separately or sequentially with another agent, including but not limited to cisplatin. The anti-neoplastic agent regimens utilized according to the invention include any regimen believed to be optimally suitable for the treatment of the patient's neoplastic condition. Different malignancies can require use of specific anti-tumor conjugates and specific anti-neoplastic agents, which will be determined on a patient to patient basis. Routes of administration include, for example, oral, intravenous, intraperitoneal, subcutaneous, or intramuscular administration. The dose and frequency of dose of antagonist administered depends on numerous factors, including, for example, the type of antagonists, the type and severity of tumor being treated and the route of administration of the antagonists. It should be emphasized, however, that the present invention is not limited to any particular method or route of administration.

The conjugate of the invention, where used in a mammal for the purpose of treatment, is preferably formulated as pharmaceutical compositions. Such pharmaceutical compositions and processes for preparing the same are well known in the art. See, e.g. Remington: The Science and Practice of Pharmacy (Gennaro A., et al., eds., 19$^{th}$ ed., Mack Publishing Co., 1995).

Patient expression levels of FGFR3 may be compared to threshold expression levels of FGFR3. These threshold levels may be taken from a variety of sources, including but not limited to, animal models of cancer, patient tumor microarray data or levels seen in a control population including a control patient population.

FGFR3 expression levels can be measured in a variety of methods including commercially available kits. Measuring FGFR3 expression levels may include, but is not limited to, measuring protein or mRNA. In one such technique, FGFR3 standards or samples are added to a plate pre-coated with antibodies to human FGFR3 ECD to allow binding of FGFR3 to antibodies. After washing unbound FGFR3 and other proteins, a horseradish peroxidase labeled anti-FGFR3 antibody is added that recognizes the FGFR3 ECD. The secondary antibody coupled to horseradish peroxidase emits a bluish color when substrate is added to the wells. The intensity of the color correlates to the quantity of FGFR3 bound specifically to the plate.

In a second such technique used to measure FGFR3 in tumor tissue or cells, standards generated from cells engineered to stably express a predefined level of FGFR3, cells that are negative for FGFR3 and/or mammal or patient samples are prepared for immunohistochemical staining. Tissues or cells are formalin fixed paraffin embedded. Fixed tissues are prepared for immunohistochemical staining on slides. Slides are incubated with primary antibodies to human FGFR3. After washing away unbound antibodies, a secondary antibody that binds to the primary antibody and is labeled with horseradish peroxidase is incubated on the slide. The secondary antibody coupled to horseradish peroxidase emits a bluish color when substrate is added to the slide. The intensity of the color correlates to the quantity of FGFR3 found in the tissue slide.

Total FGFR3-TACC3 fusion levels can be measured similarly. FGFR3-TACC3 standards or samples are added to a plate pre-coated with antibodies to human FGFR3 ECD to allow binding of FGFR3-TACC3 to antibodies. After washing unbound FGFR3-TACC3 and other proteins, a secondary antibody is added that recognizes the TACC3 protein domains that are translocated to the FGFR3 protein. The secondary antibody coupled to horseradish peroxidase emits a bluish color when substrate is added to the wells. The intensity of the color correlates to the quantity of FGFR3-TACC3 found in the plate.

Identification of the patient's FGFR3 mutational status can be measured in a variety of methods including commercially available kits. In one such technique, cells or tissue samples are lysed and the DNA is isolated. The isolated DNA is washed with 70% ethanol, dried and resuspended in water. DNA samples are then put in a PCR reaction with primers specifically designed to amplify the regions of the FGFR3 gene known to contain the mutations of interest. The resulting PCR product is purified and sequenced. FGFR3 can also be identified though next generation sequencing, real time PCR or other detection or genomic methods.

Identification of the FGFR3-TACC3 fusion status can be measured in a variety of methods including commercially available kits. In one such technique cells or tissue samples are lysed and total RNA is isolated. The isolated total RNA is then used to synthesize cDNA. Specific PCR primers designed to amplify the region containing the FGFR3-TACC3 fusion sequence are then used with the cDNA in a PCR reaction. The PCR reaction is then run on a gel used to separate PCR product. The gel is run with standards generated from transfected cell lines harboring the fusion. The FGFR3-TACC3 fusion can also be detected with standard real time PCR and fluorescent in situ hybridization (FISH) assays.

Measurements or detection of the expression levels of FGFR3, mutations of FGFR3, fusions of FGFR3, or combinations thereof, can be completed simultaneously, separately or sequentially. The measurements or detection can occur with a variety of techniques including multimodal high throughput PCR.

The present invention also includes kits for inhibiting tumor growth and/or angiogenesis comprising a therapeutically effective amount of a conjugate. The kits can further comprise the conjugate and an additional anti-cancer agent, including anti-neoplastic agents or treatments, including but not limited to cisplatin. Alternatively, or in addition to, the kits can contain any suitable antagonist of, for example, another growth factor receptor involved in tumorgenesis or angiogenesis discussed infra including EGFR. The kits of the present invention can further comprise an adjuvant.

Accordingly, Conjugate 1 can be used in vivo and in vitro for investigative, diagnostic, or treatment methods, which are well known in the art. Variations in the principles of invention herein disclosed can be made by one skilled in the art and it is intended that such modifications are to be included within the scope of the present invention.

It is to be understood and expected that variations in the principles of invention herein disclosed can be made by one skilled in the art and it is intended that such modifications are to be included within the scope of the present invention.

EXAMPLES

The following examples further illustrate the invention, but should not be construed to limit the scope of the invention in any way. Detailed descriptions of conventional methods, such as those employed in the construction of vectors and plasmids, the insertion of genes encoding polypeptides into such vectors and plasmids, the introduction of plasmids into host cells, and the expression and determination thereof of genes and gene products can be obtained from numerous publications, including Sambrook, J. et al., Molecular Cloning: A Laboratory Manual, 2nd ed., Cold Spring Harbor Laboratory Press (1989) and Coligan, J. et al. Current Protocols in Immunology, Wiley & Sons, Incorporated (2007).

Expression and Purification of Human Anti-FGFR3 Antibodies for Conjugate 1

For each antibody, engineer a suitable heavy chain nucleotide sequence, for example SEQ ID NO. 12 for Antibody 1 into a suitable expression plasmid, for example pGSHC, and engineer a suitable light chain nucleotide sequence, for example SEQ ID NO. 13 for Antibody 1 into a suitable expression plasmid, such as pGSLC, by a suitable method such as PCR cloning. To establish a stable cell line, cotransfect in a suitable host cell line, such as NS0 or CHO cells, with linearized heavy and light chain plasmids by electroporation and culture in suitable media such as glutamine free Dulbecco's Modified Eagle Medium with dialyzed fetal calf serum and glutamine synthetase supplement. Screen clones for antibody expression by an enzyme-linked immunosorbent assay (ELISA) and select the highest producer for culture in spinner flasks. Purify antibodies by a suitable method such as protein-A affinity chromatography.

Table 1 provides the amino acid sequences and SEQ ID NOs of Antibody 1 of Conjugate 1 of the present invention. All CDR sequences are determined using the AbM definition.

TABLE 1

Amino Acid Sequence of Antibody 1 of Conjugate 1 of the Present Invention

|  | Heavy Chain | SEQ ID NO. | Light Chain | SEQ ID NO. |
|---|---|---|---|---|
| CDR1 | GYMFTSYGIS | 1 | GGNNIGDKSVH | 4 |
| CDR2 | WVSTYNGDTNYAQKFQG | 2 | LDTERPS | 5 |
| CDR3 | VLGYYDSIDGYYYGMDV | 3 | QVWDSGSDHVV | 6 |
| Variable Region | EVQLVQSGAEVKKPGASV KVSCKASGYMFTSYGISW VRQAPGQGLEWMGWVST YNGDTNYAQKFQGRVTV TTDTSTSTAYMELRSLRSE DTAVYYCARVLGYYDSID GYYYGMDVWGQGTTVT VSS | 7 | QSVLTQPPSLSVAPGKT ATFTCGGNNIGDKSVH WYRQKPGQAPVLVMYL DTERPSGIPERMSGSNFG NTATLTITRVEAGDEAD YYCQVWDSGSDHVVFG GGTKLTVLG | 8 |
| Full Length | EVQLVQSGAEVKKPGASV KVSCKASGYMFTSYGISW VRQAPGQGLEWMGWVST YNGDTNYAQKFQGRVTV TTDTSTSTAYMELRSLRSE DTAVYYCARVLGYYDSID GYYYGMDVWGQGTTVT VSSASTKGPSVFPLAPSSK STSGGTAALGCLVKDYFP EPVTVSWNSGALTSGVHT | 9 | QSVLTQPPSLSVAPGKT ATFTCGGNNIGDKSVH WYRQKPGQAPVLVMYL DTERPSGIPERMSGSNFG NTATLTITRVEAGDEAD YYCQVWDSGSDHVVFG GGTKLTVLGQPKAAPSV TLFPPSSEELQANKATLV CLISDFYPGAVTVAWKA DSSPVKAGVETTTPSKQ | 10 |

TABLE 1-continued

Amino Acid Sequence of Antibody 1 of Conjugate 1 of the Present Invention

| Heavy Chain | SEQ ID NO. | Light Chain | SEQ ID NO. |
|---|---|---|---|
| FPAVLQSSGLYSLSSVVTV PSSSLGTQTYICNVNHKPS NTKVDKRVEPKSCDKTHT CPPCPAPELLGGPSVFLFP PKPKDTLMISRTPEVTCVV VDVSHEDPEVKFNWYVD GVEVHNAKTKPREEQYNS TYRVVSVLTVLHQDWLN GKEYKCKVSNKALPAPIE KTISKAKGQPREPQVYTLP PSREEMTKNQVSLTCLVK GFYPSDIAVEWESNGQPE NNYKTTPPVLDSDGSFFL YSKLTVDKSRWQQGNVF SCSVMHEALHNHYTQKSL SLSPGK | | SNNKYAASSYLSLTPEQ WKSHRSYSCQVTHEGST VEKTVAPAECS | |

Method of Conjugation of Conjugate 1

The conjugate of the present invention can be prepared by a variety of methods known in the art, such as those described in U.S. Pat. Nos. 7,811,572, 8,383,122, 6,441,163, 7,368,565, 8,163,888, and US application publication Nos 2011/0003969, 2011/0166319, 2012/0253021 and 2012/0259100. The above disclosed methods vary in the amount of yield, purity, monomers, aggregates, percent of free Maytansinoid, fragmentation, etc. that results. Selection of an appropriate conjugation method depends on the requirements of the end user.

In one aspect of the invention, conjugate Antibody 1 to DM4 using the sulfo-SPDB linker using the general method set forth in 2012/0253021 for the "one-step" process. More specifically, concentrate the Antibody 1 to 10 mg/mL and diafilter into reaction buffer. Mix Antibody 1 at 10 mg/mL with 5.6 moles DM4 relative to antibody in buffer with 50 mM 4-(2-Hydroxyethyl)-1-piperazinepropanesulfonic acid (EPPS), 20 mM sodium chloride, 2 mM EDTA pH 8.2 supplemented with 9% DMA (v/v). Conjugate Antibody 1 in this mixture by adding 5.1 moles of sulfo-SPDB and react at 15° C. for 20 hours. Adjust the pH of the conjugation mixture to 5.0 with acetic acid, concentrate to 20 mg/mL, diafiltered against 12 diavolumes of buffer containing 10 mM sodium acetate at pH 5.0. Formulate the conjugate at 5.0 mg/mL in buffer containing 10 mM acetate, 9% sucrose (w/v), 0.01% (w/v) polysorbate 20, pH 5.0.

UV Determination of DAR of Conjugate 1

Evaluate the DAR of DM4 to Antibody 1 in Conjugate 1, using Conjugate 1 material as prepared above using ultraviolet absorption.

Calculate DAR by measuring the absorption of the conjugate at 252 nm and 280 nm. Using the extinction coefficient for both DM4 and the antibody at these wavelengths, the concentration of total DM4 and antibody in the solution is measured. The DAR is defined by the ratio of moles of DM4/moles of antibody.

Determine sample concentration using a Beckman Coulter® DU800 spectrophotometer by measuring the absorption of the conjugate solution at 280 nm and 252 nm in a 1 cm pathlength quartz cuvette. Record a measurement in a non-absorbing region (320 nm) to assure that light scatter does not impact the absorption reading at the target wavelengths. Dilute samples with buffer such that the 280 nm absorbance result is in the linear range of the instrument (absorbance target 0.7-1.5 (or 0.5 to 0.9 g/L)), and the appropriate dilution factor is used in the concentration calculation. Determine concentration by the following equations:

Molar concentration of DM4, $C_{DM4}(M)$: Equation (1)
$$C_{DM4}(M) = \frac{A_{252} - 0.35 \times A_{280}}{24166}$$

Molar concentration of Conjugate 1, $C_A(M)$: Equation (2)
$$C_A(M) = \frac{A_{280} - 5323 \times C_{DM4}}{240,360} \text{ or}$$
$$C_A(M) = \frac{4.89 \times A_{280} - A_{252}}{1,091,234}$$

Concentration of Conjugate 1, $C_A$(mg/mL): Equation (3)
$$C_A(\text{mg/mL}) = C_A(M) \times 145,600$$

Maytansinoid-to-Antibody Ratio, DAR: Equation (4)
$$DAR = \frac{C_{DM4}(M)}{C_A(M)}$$

Abbreviations:
$C_{DM4}$: Concentration of DM4
$C_A$: Concentration of Antibody 1
DAR: Maytansinoid to antibody ratio
$A_{280}$: Absorbance at 280 nm
$A_{252}$: Absorbance at 252 nm
$\epsilon_{280}$: Extinction coefficient at 280 nm
$\epsilon_{252}$: Extinction coefficient at 252 nm
Constants for DM4:
$\epsilon_{DM4,252}$: 26010 $M^{-1}cm^{-1}$
$\epsilon_{DM4,280}$: 5323 $M^{-1}cm^{-1}$
Extinction coefficient ratio 252 nm/280 nm, $\epsilon_{252}/\epsilon_{280}$: 4.89
Molecular weight: 780.4 g/mol
Constants for D11 antibody:
$\epsilon_{A,280}$: 1.7 mL/(mg*cm) or 240,360 $M^{-1}cm^{-1}$
Extinction coefficient ratio 252 nm/280 nm, $\epsilon_{252}/\epsilon_{280}$: 0.35
Molecular weight: 145.6 kDa Equation 1 determines the concentration of DM4 in the solution by subtracting the absorption due to the antibody at 252 nm. Equation 2 determines the concentration of the antibody by subtracting the absorption due to the DM4. DAR is determined by calculating the ratio of the DM4 and antibody concentrations (equation 4).

Determine the monomer by size exclusion HPLC, in isocratic mode with 170 mM potassium phosphate, 212 mM potassium chloride, pH 7.0, supplemented with 15% (v/v) isopropanol. Inject 150 μg of the conjugate. Monitor the elution at 280 nm. Calculate aggregates as the summed area of all peaks eluting before the main peak. Calculate low molecular weight species as the summed area of all resolved peaks eluting later than the main peak.

Measure free maytansinoid levels by dual column SEC/reverse phase HPLC. Prepare conjugate solution with 20% acetonitrile, incubated at room temperature for 30 minutes, and stored at 5° C. prior to analysis. Inject the conjugate onto a size exclusion column (SEC), where the conjugated antibody is washed through the column. Once the conjugate is eluted, redirect the column effluent to a C-18 column where the remaining small molecules bind, and are eluted by a gradient program (20% acetonitrile with 0.1% TFA/80% water with 0.1% TFA) over 35 minutes. Sum the peak areas. Determine the DM4 content using the slope from a standard curve. Percent free maytansinoid is the ratio of moles of free DM4 (determined by this dual column HPLC method) over moles of total DM4 (determined by the UV DAR method) multiplied by 100.

TABLE 2

| DAR | |
|---|---|
| Yield | 89.2% |
| Concentration | 4.9 |
| DAR (UV) | 3.5 |
| Free Maytansinoid (% vs. total DM4) | 0.7% |

The DAR of a representative lot of Conjugate 1 was 3.5±0.5.

Binding Kinetics and Affinity to Human FGFR3 Analysis by Surface Plasmon Resonance Assay (Biacore®)

Determine binding affinity and binding stoichiometry to human FGFR3(IIIb), a splice form of FGFR3, using a surface plasmon resonance assay on a Biacore® T200 instrument primed with running buffer and analysis temperature set at 25° C. Use a CM5 chip containing immobilized receptor huFGFR3(IIIb) (generated using standard NHS-EDC amine coupling) on 2 flow cells. Prepare samples of Conjugate 1 by 2 fold serial dilutions starting at 60 nM, 6 dilutions total into running buffer. Immobilize receptor at 2.5 μg/mL (55 RU). Each analysis cycle consists of: (1) sample injection at 30 μL/min with 180 sec contact time, (2) dissociation by injection of buffer for 900 sec at 30 μL/min, (3) regeneration in a 0.5% solution of SDS contact time 30 sec at a flow rate of 40 μL/min. Process data using standard double-referencing and fit to a 1:1 binding model using Biacore® 2000 Evaluation software, version 4.1, to determine the association rate ($k_{on}$, $M^{-1}s^{-1}$ units), dissociation rate ($k_{off}$, $s^{-1}$ units), and Rmax (RU units). The equilibrium dissociation constant ($K_D$) is calculated from the relationship of $K_D = k_{off}/k_{on}$. $K_D$ is in molar units.

Antibody 1 has a $K_D$ of $1.3 \times 10^{-10}$ M. Conjugate 1 binds to huFGFR3(IIIb) with an average association rate ($k_{on}$) of $(2.27 \pm 0.001) \times 10^5$ and dissociation rate ($k_{off}$) of $(1.87 \pm 0.13) \times 10^{-4}$. Table 1 shows a summary of the experimental results with calculated standard deviations from n=3 independent experiments. Conjugate 1 binds to huFGFR3(IIIb) under physiological pH and ionic strength with a $K_D$ of $(8.23 \pm 0.59) \times 10^{-10}$ M.

TABLE 3

Conjugate 1 Binding Kinetics and Affinity to human FGFR3(IIIb)

| Antigen | $K_{on}$ (1/Ms) | $K_{off}$ (1/s) | $K_D$ (M) |
|---|---|---|---|
| huFGFR3(IIIb) | $(2.27 \pm 0.001) \times 10^5$ | $(1.87 \pm 0.13) \times 10^{-4}$ | $(8.23 \pm 0.59) \times 10^{-10}$ |

Accordingly, conjugation does not alter the ligand binding functionality of the naked, non-conjugated antibody.

Enzyme-Linked Immuno Absorbent (ELISA) Assays

Conjugate 1 Blocking of FGF1 Ligand Binding to Human FGFR3(IIIb)

Spot coat a standard 96 well Multi-Array® plate (Meso Scale Discovery® (MSD®) #L15XA-6) with 100 ng per well of human FGFR3(IIIb)-Fc (5 μL/well of 20 μg/mL solution in PBS), cover and incubate overnight at room temperature. To block non-specific binding in the wells, add 150 μL of 5% MSD® Blocker A (R93BA-1) to each well and incubate for 1 hour at room temperature. In a separate 96 well ELISA plate, prepare 1:3 serial dilutions of test articles starting at 1 μg/mL in PBS, 0.05% Tween® 20 (PBS-T), 1% BSA. Discard the blocker and transfer 30 μL per well of these dilutions into the appropriate wells of the coated and blocked MSD® plate and gently agitate for 1 hour at room temperature. Decant the plate and wash twice with 200 μL/well PBS-T. Add 30 μL per well of 1 μg/mL ruthenium-labeled FGF1 in PBS-T, 1% BSA, 10 μg/mL heparin (Sigma cat # H3149-50KU) to the plate and gently agitate for 1 hour at room temperature in the dark. Decant the plate again and wash twice with 200 μL/well PBS-T. After washing, add 150 μL of 1×MSD® Read Buffer (MSD®, #R92TC-2) to each well. Upon electrochemical stimulation, ruthenium label on the bound FGF-1 emits luminescent light at 620 nm. Detect ECL signals by a charge-coupled device camera in a SECTOR® Imager 2400 plate reader (MSD®, #1250). Plot electrochemiluminescence, measured as relative light units (RLU), in GraphPad Prism® software version 6.0. Calculate $IC_{50}$ values by nonlinear regression curve fit analysis utilizing the software's log [inhibitor] vs. response function.

Conjugate 1 blocks FGF1 binding to FGFR3 with an $IC_{50}$ of 3.6 nM, which supports that in addition to binding FGFR3, Conjugate 1 is also function blocking in that it blocks cognate (FGF1) ligand binding to FGFR3.

Antibody 1 Blocking FGF1 and FGF9 Binding to FGFR3

Assess the ability of Antibody 1, the antibody component of Conjugate 1, to neutralize ligand induced proliferation of cell lines harboring various forms of FGFR3, including mutations, fusions and wild type (WT).

BaF3 is a mouse pro-B cell line that is dependent on mouse IL-3 for survival. When receptors are introduced into BaF3 cells, they can proliferate in response to the receptor ligands, without the need for exogenous IL-3.

Prepare BaF3 cell lines expressing either wild type or mutant human FGFR3 by retroviral transduction. Each line is a puromycin-resistant stable pool. Maintain cell lines in BaF3 culture medium (containing mouse IL-3 and puromycin) at a cell density of 20,000 to 1,000,000 cells/mL and dilute every 1-4 days with fresh culture medium. Dilute BaF3+FGFR3 cells used in $^3$H thymidine incorporation assays to 20 to 50,000 cells/mL 1 to 3 days before an assay. For the assay, cell culture density is between 100,000 and 1,000,000 cells/mL. Initially, test FGF-1 (FGF acidic) and/or FGF-9 for dose-dependent stimulation of $^3$H thymidine incorporation in BaF3+FGFR(III3b) WT, +FGFR3(IIIc) WT cells and compare to BaF3+MSCV empty vector control cells. Centrifuge BaF3 lines at 1,000 rpm for 3 minutes at RT and wash 3 times with 20 mL BaF3 assay medium (centrifuging the same way after each wash). Add 100 µL of BaF3+FGFR3(IIIb) WT, +FGFR3(IIIc) WT, or +empty vector cell lines at 200,000 cells/mL or 800,000 cells/mL (20,000 or 80,000 cells/well) to the inner 60 wells of 96-well tissue culture plates (BD Falcon™ No. 35-3072). Add 50 µL of 4× heparin (final concentration 5 or 10 µg/mL) (or assay medium) to the wells. Serially dilute FGF-1 or FGF-9 (1:2-1:5) in assay medium (in polypropylene plates). Add 50 µL of 4×FGF-1, 4×FGF-9, or assay medium alone, to the wells (in triplicate). Add 250 µL of assay medium or Dulbecco's PBS to the edge wells to reduce evaporation. Incubate cells for 72 hours at 37° C., 5% CO2 and 95% RH. Add 20 µL of 0.1 mCi/mL thymidine-[methyl-$^3$H] in D-PBS (MP Biomedicals No. 2406605) per well for the last 6 hours of incubation. Freeze assay plates at −80° C., thaw at 37° C., and harvest onto UniFilter-96, GF/C plates (Perkin Elmer No. 6005174) using a Filtermate™ Harvester (Packard). Dry UniFilter plates and add 20 µL of Microscint-0 scintillant (Perkin Elmer No. 6013611) per well. Count incorporated $^3$H thymidine on the filter plates for 1 minute per well on a 1450-021 Microbeta liquid scintillation counter (Wallac). To evaluate Antibody 1 for neutralization of FGF-1 or FGF-9 activity on wild type FGFR3 or mutant FGFR3, use constant amounts of human FGF-1 or human FGF-9 (FGF-1: 80 ng/mL on FGFR3(IIIc) expressing cells, 800 ng/mL on FGFR3(IIIb) expressing cells; FGF-9: 100 ng/mL on FGFR3 (IIIc) expressing cells, 800 ng/mL on FGFR3(IIIb) expressing cells.) These concentrations of FGF-1 or FGF-9 provide for at least a 2-fold increase in $^3$H-thymidine incorporation, compared to assay medium alone. To convert concentration values from µg/mL to nM, use the following formula:

Concentration in µg/mL×conversion factor=Concentration in nM where the conversion factor is inversely proportional to MW (molecular weight); 6.667 is the conversion factor for a monoclonal antibody, assuming the MW is 150 kD. FGF-1: molecular weight=15.5 kD, therefore the conversion factor is 64.45. FGF-9: molecular weight=23 kD, therefore the conversion factor is 43.

Centrifuge BaF3 lines (between 2 and 8 passages after gaining puromycin resistance) at 1,000 rpm for 3 minutes at RT and wash 3 times with 20 mL BaF3 assay medium. Add 50 µL of BaF3 cells expressing FGFR3(IIIb) WT, FGFR3(IIIc) WT, FGFR3(IIIb) mutants or FGFR3(IIIc) mutants, at 400,000 cells/mL (20,000 cells/well) to the inner 60 wells of 96-well tissue culture plates (BD Falcon™). In a separate dilution plate (polypropylene), dilute Antibody 1 or human IgG1 isotype control antibody (to 4× the top working concentration) in assay medium. Further serially dilute (1:3) the antibodies in assay medium. Add 50 µL of each test concentration of the antibody to wells containing BaF3 cells. Test using triplicate wells per treatment. Instead of antibodies, add 50 µL of assay medium for "medium alone" and "FGF alone" controls. Incubate plates containing cell and antibody mixtures for 45 minutes at 37° C., 95% RH, 5% CO$_2$, before the addition of heparin and FGF. Add 50 µL of 4× heparin (final concentration 10 µg/mL) to all wells. Add 50 µL of 4×FGF-1 or 4×FGF-9 (diluted in assay medium), or assay medium alone, to the wells (in triplicate). Add 250 µL of assay medium to the edge wells to reduce evaporation. Incubate cells for 72 hours (cells expressing FGFR3(IIIc) WT or mutants) to 96 hours (cells expressing FGFR3(IIIb) WT or mutants) at 37° C., 5% CO$_2$ and 95% RH. Add 20 µL of 0.1 mCi/mL thymidine-[methyl-$^3$H] in D-PBS (MP Biomedicals No. 2406605) per well for the last 6 hours of incubation. Harvest incorporated $^3$H-thymidine and count as described above using a 1450-021 Microbeta liquid scintillation counter.

TABLE 4

IC$_{50}$ Values of Antibody 1 for Neutralizing FGF1 or FGF9 on Wild Type or Mutant Human FGFR3

| Receptor Isoform/Mutation | Ligand (Concentration) | AVG IC$_{50}$ (nM) |
|---|---|---|
| FGFR3(IIIb) WT | FGF1 (51.6 nM) | 4.20 |
| FGFR3(IIIb) R248C | FGF1 (51.6 nM) | 1.32 |
| FGFR3(IIIb) S249C | FGF1 (51.6 nM) | 2.17 |
| FGFR3(IIIb) G372C | FGF1 (51.6 nM) | 4.81 |
| FGFR3(IIIb) Y375C | FGF1 (51.6 nM) | 8.77 |
| FGFR3(IIIc) WT | FGF1 (5.16 nM) | 11.86 |
| FGFR3(IIIc) S249C | FGF1 (5.16 nM) | 30.4 |
| FGFR3(IIIc) K650E | FGF1 (5.16 nM) | 8.11 |
| FGFR3(IIIb) WT | FGF9 (34.72 nM) | 0.40 |
| FGFR3(IIIb) R248C | FGF9 (34.72 nM) | ND |
| FGFR3(IIIb) S249C | FGF9 (34.72 nM) | 0.46 |
| FGFR3(IIIb) G372C | FGF9 (34.72 nM) | ND |
| FGFR3(IIIb) Y375C | FGF9 (34.72 nM) | 1.42 |
| FGFR3(IIIc) WT | FGF9 (4.34 nM) | 1.41 |
| FGFR3(IIIc) S249C | FGF9 (4.34 nM) | 1.50 |
| FGFR3(IIIc) K650E | FGF9 (4.34 nM) | 2.07 |

AVG = average;
IC$_{50}$ = half-maximal inhibitory concentration;
ND = not determined;
WT = wild type.
Note:
IC$_{50}$ value calculations for Antibody 1-neutralizing FGF1- or FGF9-induced $^3$H-thymidine incorporation in BaF3 cells expressing human FGFR3(IIIb) WT, FGFR3(IIIc) WT, or FGFR3 mutations.

In Table 4, Antibody 1, the antibody component of Conjugate 1, effectively neutralizes FGF1 and FGF9 ligand induced proliferation of cell lines harboring WT and mutated FGFR3 receptor.

Cytotoxicity Studies

Cytotoxicity of Conjugate 1 on Tumor Cell Lines Overexpressing FGFR3

To determine the cytotoxicity of Conjugate 1, establish the relative FGFR3 cell surface density for bladder tumor and multiple myeloma cell lines expressing FGFR3.

Culture cell lines for 48 hours, harvest with Gibco® Cell Dissociation Buffer (enzyme-free) (Gibco®, #13151-014), and count the cells. Centrifuge the cells at 1000 rpm for 5 minutes, wash once with cold PBS, pH 7.4, and resuspend at 2×10$^6$ cells/mL in cold PBS, pH 7.4. Block cells with 30 µg/mL human IgG in FACS (Fluorescence-activated cell sorting) staining buffer (PBS, pH 7.4, 3% BSA) in a 96 well round-bottom plate for 1 hour on ice. After blocking, centrifuge the cells at 1200 rpm for 5 minutes and remove the supernatant. Add 100 µL of FACS staining buffer to the unstained control wells. Add 100 µL of 15 µg/mL Alexa488-labeled Antibody 1 (used to monitor FGFR3 internalization), anti-KLH (non-targeted control conjugate) or chKTI antibody (non-targeted control conjugate) in FACS staining buffer to the appropriate testing wells containing cells. Add the buffer and antibodies to empty wells, and then add 2 drops of each of the standard beads solutions from the Quantum™ Simply Cellular® Beads Kit (Bangs Labs, #816B) to the appropriate wells. Incubate the plate in the dark on ice for 1 hour. Wash the cells and beads twice with FACS Wash Buffer (PBS, pH 7.4, 0.5% BSA). Resuspend the cells in 50 µL 7-Aminoactinomycin D (7-AAD) at 5 µg/mL in FACS Wash Buffer, and resuspend the beads in 50 µL FACS Wash Buffer. Read the wells on IntelliCyt® HTFC and analyze using FlowJo software. Insert the Median fluorescence intensity (MFI) values generated by FlowJo into the Excel spreadsheet provided by Bangs Lab for Antibody Binding Capacity (ABC) determination. The reported values are a result of subtraction of the non-specific ABC values determined using the anti-KLH or chKTI antibody from the specific ABC values determined using the naked Antibody 1 (see the column labeled "FGFR3 cell surface expression (ABC)" in Table 5). It is noted that the above methodology was used to determine the ABC for other cell lines discussed herein that are not explicitly listed in Table 5.

TABLE 5

Conjugate 1 Cytotoxicity in Tumor Cell Lines

| Tumor cell line | FGFR3 status | FGFR3 cell surface expression (ABC) | Cytotoxicity Conjugate 1 IC$_{50}$ | Cytotoxicity Isotype control IC$_{50}$ |
|---|---|---|---|---|
| BFTC-905 (bladder) | WT | 11,000 | 2.7 nM | NS |
| UMUC-14 (bladder) | S249C | 27,000 | 0.5 nM | NS |
| RT-112 (bladder) | WT, TACC3 fusion | 16,000 | 1.3 nM | NS |
| KU-19-19 (bladder) | WT | ≤4,000 | NS | NS |
| KMS-11 (multiple myeloma) | T(4;14) + Y373C | 120,000 | 0.04 nM | NS |

NS = not significant

A trend of increasing cytotoxicity with increasing expression of FGFR3 on the cell surface was observed. These data also support increased sensitivity to Conjugate 1 in the presence of FGFR3 mutations and/or fusions which results in enhanced cell cytotoxicity.

Cytotoxicity Testing: Antibody 1, the Antibody Component of the Present Invention, can Selectively Deliver a Cytotoxic Payload Antibody 1, the antibody component of the present invention, can selectively deliver a cytotoxic payload to tumor cells.

Plate cells in 96 well tissue culture plates at 2500 cells per well in 90 µL of complete media and incubate for 4 hours at 37° C. in a humidified atmosphere containing 5% CO$_2$. Just prior to the end of this incubation, dilute the test articles with complete media in 3-fold series dilutions in round-bottom 96 well plates. After the 4 hour incubation, mix 10 µL of the diluted antibodies with a constant amount of the conjugated Fab (10 nM), add to corresponding wells in the cell plate, and incubate for 96 hours at 37° C. in a humidified atmosphere containing 5% CO$_2$. After this incubation, remove the plates from the incubator and allow to come to room temperature for all subsequent steps. Add 100 µl of Cell Titer-Glo® reagent (Promega #TB288) to each well and incubate the plates for 2 hours, protected from light. Detect luminescence signals in a Spectra Max® M5e Multi-Mode microplate reader. Calculate the experimental wells as a percent of untreated control wells. Plot data using GraphPad Prism® 6 and determine IC$_{50}$s using the log inhibitor vs. normalized response, variable slope, analysis.

The significant cytotoxicity seen with multiple myeloma cell line KMS-11 [t(4;14), Y373C] (IC$_{50}$=0.11 nM) that expresses 120,000 antigens provides validation that Antibody 1, the antibody component of Conjugate 1, can deliver payload via engagement with FGFR3. This data suggests that cytotoxic potency increases with increasing FGFR3 antigen density and mutational status as seen when comparing across the numerous bladder tumor cell lines (RT-112 (TACC3)) expresses ~16,000 antigens vs. BFTC-905 (wild type) expresses ~11,000 antigens) and Multiple Myeloma tumor cell lines (KMS-11 [t(4;14), Y373C] expresses ~120,000 antigens vs. OPM-2 [t(4;14), K650E] expresses ~51,000 antigens vs. LP-1[t(4;14)] (wild-type) expresses ~9,000 antigens) evaluated. While an important component of conjugate cytotoxic activity is antigen density, antigen density partnered with FGFR3 mutational status may also be important in some cell lines.

TABLE 6

Potency Correlated with FGFR3 Surface Expression and FGFR3 Mutational status

| Cell Lines | IC$_{50}$ (nM) | | |
|---|---|---|---|
| (FGFR3 cell surface expression (ABC)) | Antibody 1 | Conjugate 1 | KLH-sulfo-SPDB-DM4 |
| RT112 (11,000) | NA | 2.1 | 10.0 |
| Cal-29 (16,000) | NA | 10.5 | NA |
| KMS-11 (120,000) | NA | 0.24 | NA |
| OPM-2 (51,000) | NA | 1.8 | 20.5 |
| LP-1 (9,000) | NA | NA | 15.7 |
| Kato-III (142,000) | NA | 5.4 | 19.4 |
| OE-33 (25,000) | NA | 15.0 | 16.8 |
| Baf3-FGFR3(IIIb) (48,000) | NA | 2.5 | NA |
| Baf3-FGFR3(IIIc) (20,000) | NA | 5.0 | NA |

NA = IC$_{50}$ not attained at maximum concentration of 30 nM
Cell lines: RT112 (TACC3), Cal-29 Bladder, KMS-11[t5(4:14, Y373 C], OPM-2, LP-1 Multiple Myeloma, Kato-III Gastric, OE-33 SCHNN, Baf3-FGFR3(IIIb), Baf3-FGFR3 (IIIc) transfected Bladder (RT112-TACC3), MM (KMS-11 [t(4;14)Y373C], OPM-2 [t(4;14), K650E]), Gastric Kato-III and transfected Baf3-FGFR3(IIIb), Baf3-FGFR3(IIIc) cell lines are sensitive to selective cytotoxic killing action of Conjugate 1. This potency correlates with FGFR3 surface expression and FGFR3 mutational status.

Cytotoxicity Testing of Bladder Tumor Cell Lines with Conjugate 1

Conjugate 1 is cytotoxic in numerous in vitro bladder tumor cell lines overexpressing various forms of FGFR3.

Plate cells in 96 well tissue culture plates at 2500 cells per well in 90 µL of complete media and incubate for 4 hours at 37° C. in a humidified atmosphere containing 5% CO$_2$. Just prior to the end of this incubation, dilute the test articles with complete media in 3-fold series dilutions in round-bottom 96 well plates. After the 4 hour incubation, add 10 µL of the diluted antibodies to corresponding wells in the cell plate and incubate for 96 hours at 37° C. in a humidified atmosphere containing 5% CO$_2$. After this incubation, remove the plates from the incubator and allow them to come to room temperature for all subsequent steps. Add 100 µL of Cell Titer-Glo® reagent (Promega #TB288) to each well and incubate the plates for 2 hours, protected from light. Detect Luminescence signals in a Spectra Max® M5e Multi-Mode microplate reader. Calculate the experimental wells as a percent of untreated control wells. Plot data using GraphPad Prism® 6 and determine IC$_{50}$s using the log inhibitor vs. normalized response, variable slope, analysis.

The results show significant cytotoxicity of Conjugate 1 when the molecule is used to treat each of the FGFR3 overexpressing bladder tumor cell lines (see Table 5). The compound is slightly more potent in the UMUC-14 tumor cell line, which overexpresses FGFR3 containing a mutation in the ECD, which renders the receptor constitutively active.

The negative control isotype matched conjugate shows no cytotoxicity in the concentration ranges seen with Conjugate 1 in any of the lines. Bladder tumor cell line KU-19-19, which does not overexpress FGFR3, is included in the experiment to assess non-specific cytotoxicity. Conjugate 1 is not cytotoxic to the KU-19-19 line. The results show that specific in vitro cytotoxicity can be induced by Conjugate 1 in cell lines that overexpress FGFR3 WT, FGFR3 mutants S249C or Y373C, in the absence or presence of FGFR3-TACC3 fusion receptors.

FGFR3 Internalization

Perform in vitro studies employing live cell imaging, FLOW cytometry, and various biochemical analyses, to understand the relationship between FGFR3 mutational status, surface expression, and receptor-mediated antibody internalization. Determine how these factors combine to ultimately influence conjugate cytotoxicity.

The data herein demonstrates that increased rates of FGFR3 internalization associate with mutational drivers of FGFR3, including S249C mutations and FGFR3-TACC3 fusions, and that these anomalies correlate with enhanced sensitivity to Conjugate 1. Quantitative analysis of antibody internalization is performed on a panel of cell lines that harbor a variety of mutations and express varying levels of surface FGFR3. These cell lines include: RT-4 (TACC3 exon-4, surface density antibody binding capacity (ABC) of ~29,000), UMUC-14 (S249C, ABC ~27,000), RT-112 (TACC3 exon-10, ABC ~16,000), BFTC-905 (WT, ABC ~11,000), KU-19-19 (WT, ABC ≤4,000), and UMUC-3 (WT, ABC ≤4,000) (see in part Tables 5 and 6).

Initial characterization of these lines by live cell confocal microscopy and Alexa488 fluorescently labeled antibodies demonstrates specific internalization of the anti-FGFR3 antibody, Antibody 1, as compared to a human IgG control (chKTI), in a panel of bladder cell lines.

Receptor-mediated internalization of Antibody 1-Alexa488 (67 nM) in RT-112 cells was evident at 24 hours post antibody addition. In the live cell experiment, Antibody 1 is seen to internalize into the cell.

In parallel live cell experiments, quantify delivery of antibody-receptor complexes to the lysosome with the use of a pH-activated dye (pHrodo™), which exhibits minimal fluorescence at neutral pH and increases fluorescence intensity as the pH drops. Significant increases in the accumulation of the pH-dye signal upon Antibody 1 addition, as compared with control IgG antibody, were observed and this effect is receptor mediated, as control cells that do not express FGFR3 (Baf3R2) did not yield an appreciable signal above background.

Fluorescently label Antibody 1 and the control antibody chKTI (Antibody 1-Alexa488 or chKIT-Alexa488), incubate these with the same panel of cell lines and allow the labeled antibodies to internalize over a 48 hour time period. Harvest samples at 0.5, 1, 2, 4, 6, 24, and 48 hours and quantify cell-associated fluorescence by Flow Cytometry.

The results highlight significant differences in the degree of internalization of Antibody 1-Alexa488 across the panel of cell lines. The UMUC-14 cells harboring the S249C mutation internalize the most FGFR3 antibody, greater than 9-fold over control in terms of both quantity and rate, while cell lines containing TACC3 fusions, RT-112 and RT-4, internalize Antibody 1-Alexa488 at approximately 7-fold over background. BFTC-905, KU-1919 and UMUC-3, which represent low expressing wild type cell lines, demonstrate little to no appreciable internalization of Antibody 1. These data illustrate that surface receptor density is only one determinant of antibody internalization; the data emphasize that the activating FGFR3 mutations and/or FGFR3-TACC3 fusion proteins in receptor trafficking and conjugate induced cytotoxicity may play a key role in internalization.

Efficacy Models

Evaluate the anti-tumor activity of Conjugate 1 in multiple tumor xenograft models, including both cell line and patient derived models, and compare to the non-conjugated naked antibody, Antibody 1. Controls consist of vehicle or non-specific antibody treated controls; chKTI or KLH and non target controls, chKTI-sulfo-SPDB-DM4 or KLH-sulfo-SPDB-DM4.

Treatment with Conjugate 1 exhibits anti-tumor activity resulting in tumor regression or stasis in a number of human bladder and multiple myeloma xenografts with a diverse FGFR3 antigen expression pattern. In each study, Conjugate 1 shows superior antitumor efficacy compared to naked Antibody 1. Treatment inhibits tumor growth by induction of tumor cell apoptosis as monitored by cleaved caspase 3 induction.

Utilize animal research methods approved by the Institutional Animal Care and Use Committee and performed in accordance with current regulations and standards of the United States Department of Agriculture and the National Institute of Health.

Generate xenograft models following implantation of human bladder carcinoma or multiple myeloma cell lines either in HBSS or as a mixture with 50% Matrigel, or following implantation of fresh 3-4 mm tumor fragments into the flank of female immunodeficient (athymic) or NOD/SCID Gamma (NSG) mice. Perform tumor fragment preparation and implantations using aseptic techniques according to the approved IACUC protocol guidelines.

When tumors reach a specified size (typically 200-300 mm$^3$), randomize the tumor-bearing mice by tumor volume and divide into one of the treatment groups, typically including vehicle, chKTI or KLH antibody control, Antibody 1 (naked mAb control), KLH-sulfo-SPDB-DM4 or chKTI-sulfo-SPDB-DM4 (non-targeted-conjugate control) and Conjugate 1. Test articles are administered intravenously (i.v.) through bolus tail vein injection either on a single or repeated (typically weekly or every other week) dosing schedule. In the majority of studies, collect EDTA plasma and tumor tissues at specific time points to measure compound exposure and apoptosis markers, respectively. Determine Conjugate 1 plasma concentrations using three different ELISAs: one that is specific for the antibody portion of the conjugate (Total Assay), one that recognizes both the antibody portion and maytansine payload (Conjugate Assay), and one that detects free maytansine (Free Assay). In brief, for the Total Assay, capture the molecule with FGFR3(IIIb) and detect using an anti-human IgG molecule. For the Conjugate Assay, capture the molecule with FGFR3(IIIb). Detect the conjugate using an anti-maytansine antibody, thus this assay is sensitive to the payload:antibody ratio. In the Free Assay, first precipitate all protein from the sample using acetone while the free maytansine remains in the supernatant. Remove the supernatant and analyze in a competition ELISA.

Analyze collected tumor tissues for cleaved caspase-3 using MSD®. Lyse snap-frozen tumor fragments (approximately 100-200 mm$^3$) using the Qiagen TissueLyser II. Normalize clarified lysates for protein concentration using the Hamilton STAR liquid handler and stamp into MSD® plates for analysis. Perform the MSD® CC3 according to the manufacturer's protocol using separate 384-well plates for Cleaved Caspase-3 as well as total Caspase-3 (express results as a ratio of cleaved/total). Following the blocking and incubation steps, wash the plates using the BioTek EL406™ plate washer and analyze using the Mesoscale Sector® 2400 imager. For data analyses, including 1-way ANOVA statistical analysis, use Graphpad Prism® software.

Measure tumor volumes with calipers and record body weights at least twice per week, initially, and then follow by weekly measurements. Tumor volumes are calculated by the formula Volume=[(Pi/6)l×w$^2$], wherein Pi equals 3.14, w represents width and l represents length. Determine the duration of treatment by: 1) pre-determined (e.g., termination for histological analysis in mechanism of action studies), 2) a study endpoint is reached (i.e., statistically significant inhibition of tumor growth is achieved, or no anti-tumor effect is apparent), or 3) a clinical endpoint is reached (e.g., tumor burden is impacting animal welfare or survival).

Express the antitumor efficacy of the experimental treatments as the T/C ratio (in percent and calculated as summarized below.

% $T/C = 100 \times \Delta T/\Delta C$, if $\Delta T > 0$ where $\Delta T$=mean tumor volume of the drug-treated group on the final day of the study minus mean tumor volume of the drug-treated group on initial day of dosing; $\Delta C$=mean tumor volume of the control group (specified in each study) on the final day of the study minus mean tumor volume of the control group on initial day of dosing. If $\Delta T<0$, calculate Regression (% Reg) instead of % T/C using the formula=$100 \times \Delta T/T$ initial. If a tumor achieves a ≥50% regression, it is a partial response (PR). If undetectable, then the tumor has a complete response (CR). To compare tumor growth between groups, use a repeated-measures analysis of variance (RM ANOVA) through the final day to determine the p value (P) using the JMP Statistical Discovery Package (V. 9, SAS Institute Inc. Cary, N.C.).

Table 7 summarizes the tumor xenograft models tested herein. The FGFR3 Receptor Density (ABCs) reproduced below were reported in Table 5.

TABLE 7

Summary of Xenograft Models Tested

| Model | Tumor Type/Pathology | Genetic Status | FGFR3 Receptor Density (ABCs) |
|---|---|---|---|
| RT-112 | Bladder UCC/R3 driver | FGFR3-TACC3, NRAS | 16,000 |
| UMUC-14 | Bladder UCC | S249C | 27,000 |
| BFTC-905 | Bladder UCC/papillar | WT, NRAS, TP53 | 11,000 |
| KU-19-19 | Bladder UCC | WT | <4,000 |
| KMS11 | Multiple Myeloma | T(4;14)+Y373C | 120,000 |

Conjugate 1 Efficacy in a RT-112 Human Bladder Xenograft Model

Perform three independent studies in the RT-112 (FGFR3-TACC3) human bladder xenograft model to evaluate antitumor efficacy and durability of the response after repeated i.v. dosing of Conjugate 1. RT-112 (FGFR3-TACC3) is a human bladder carcinoma cell line expressing 16,000 receptors as determined by FACS/BANGS analysis, which harbors the recently reported FGFR3-TACC3 gene fusion.

Randomize mice by tumor volume when achieving an average tumor volume range of 220-270 mm$^3$. Following the randomization, dose animals with tumor xenografts (n=6 to 12/group) with either vehicle control (10 µL/g; 10 mM Tris, 80 mM NaCl, 3.5% sucrose, 0.01% Tween-20, pH 7.5), KLH, control Antibody 1, KLH-sulfo-SPDB-DM4, or Conjugate 1.

In these studies, include a separate group of PK/PD cohort animals (n=4) to study the mechanism of action. In these studies, administer a single i.v. dose of KLH-sulfo-SPDB-DM4 dosed at 5 mg/kg or Conjugate 1 dosed at 2.5 and 5 mg/kg and euthanize animals at 24 and 96 hours for plasma and tumor tissue. Evaluate plasma samples for the compound plasma concentrations, and analyze tumor tissues for apoptosis markers.

In RT-112 Study 1, animals with tumor fragment xenografts (n=6/group) receive a total of 2 i.v. doses separated by a 14 day interval of either Vehicle control (10 µL/g; 10 mM Tris, 80 mM NaCl, 3.5% sucrose, 0.01% Tween-20, pH 7.5), KLH-sulfo-SPDB-DM4 (5 mg/kg), or Conjugate 1 (5 mg/kg) following randomization.

As shown in Table 8, Conjugate 1, at a dose of 5 mg/kg inhibits the growth of RT-112 tumors resulting in a complete response (CR) in 6 of 6 (100%) of animals by day 99 and 86% regression on day 154 (5 of 6 complete regression) following two i.v. doses. Of these 6 animals, 4 of 5 surviving mice remain tumor-free through day 211 while observe a tumor regrowth in a single animals. A dose of 5 mg/kg of KLH-sulfo-SPDB-DM4 results in a CR in 2 of 6 animals.

In RT-112 Study 2, a repeat dosing efficacy study, tumor-bearing mice generated after cell implantation (n=12/group) receive a total of 3 i.v. doses (days 13, 35 and 49) of USP saline (10 µl/g), Antibody 1 (10 mg/kg), KLH-sulfo-SPDB-DM4 (5 mg/kg) or Conjugate 1 (5 mg/kg). In this study, Conjugate 1 dosed at 5 mg/kg results in 44% tumor regression as compared to vehicle controls (p<0.0001) on day 47 following 2 doses. The response is maintained more than 100 days following the final dose where 9 of 12 animals achieve a complete response (CR). KLH-sulfo-SPDB-DM4 dosed at 5 mg/kg results in a T/C of 46% as compared to the saline control (p=0.02). Conjugate 1 is significantly more efficacious than naked Antibody 1 where the comparator naked Antibody 1 dosed at 10 mg/kg results in a T/C of 55%.

In RT-112 Study 3, a dose-response study (n=8/group) in which antitumor efficacy of Conjugate 1 is evaluated at 1.25, 2.5 and 5 mg/kg after a total of 5 i.v. doses (days 21 and 35 followed by 3 weekly doses). The controls in the study are KLH at 10 mg/kg, Antibody 1 at 10 mg/kg and KLH-sulfo-SPDB-DM4 at 5 mg/kg. A cohort of PK/PD animals (n=4) receive a single i.v. dose of KLH-sulfo-SPDB-DM4 at 5 mg/kg or Conjugate 1 at 2.5 and 5 mg/kg.

Conjugate 1 dosed at 2.5 or 5 mg/kg results in tumor regression corresponding to 93% and 100% (at day 82) respectively. The results show a complete response in 2/5 at 1.25 mg/kg, and 8/8 animals each following dosing at 2.5 and 5 mg/kg respectively, through day 166. Conjugate 1 dosed at 1.25 mg/kg results in tumor stasis. KLH-sulfo-SPDB-DM4 dosed at 5 mg/kg results in tumor stasis with complete regression in 2/7 animals and the effect was statistically significant as compared to the vehicle controls (p=0.02). Regressed tumors did not re-grow during the observation period (>160 days).

TABLE 8

Summary of RT-112 Human Bladder Xenograft Model

| Model | N | Treatment | Total Dose/Schedule | % T/C | Reg. (%) | CR/PR | P Value |
|---|---|---|---|---|---|---|---|
| RT-112 (TF) (RT-112 Study 1) | 6 | Vehicle | 2 (days 56 and 70) | NA | NA | NA | NA |
| | | KLH-SPDB-DM4 (5 mg/kg) | | 25 | NA | 2/6 CR | 0.37* |
| | | Conjugate 1 (5 mg/kg) | | NA | 86 CR | 5/6 | 0.055* |
| RT-112 (Matrigel+) (RT-112 Study 2) | 12 | USP Saline | 3 (days 13, 35, 49) | NA | NA | NA | NA |
| | | Antibody 1 (10 mg/kg) | | 55 | NA | NA | 0.08* |
| | | KLH-sulfo-SPDB-DM4 (5 mg/kg) | | 46 | NA | 2/12 CR, 3/12 PR | 0.02* |
| | | Conjugate 1 (5 mg/kg) | | NA | 44 | 9/12 CR 2/12 PR | <0.0001* |
| RT-112 (Matrigel+) (RT-112 Study 3) | 8 | KLH (10 mg/kg) | 5 (days 21 and 35 followed by 3 weekly doses) | NA | NA | NA | NA |
| | | Antibody 1 (10 mg/kg) | | 83 | NA | NA | 0.86* |
| | | KLH-sulfo-SPDB-DM4 (5 mg/kg) | | 6 | NA | 2/7 CR | 0.02* |
| | | Conjugate 1 (1.25 mg/kg) | | 5 | NA | 2/5 CR | 0.03* |
| | | Conjugate 1 (2.5 mg/kg) | | NA | 93 | 8/8 CR | 0.004 * |
| | | Conjugate 1 (5.0 mg/kg) | | NA | 100 | 8/8 CR | 0.008* |

*Comparison to the Vehicle, USP Saline or KLH control
NA: Not Applicable

Evaluate plasma samples for the compound plasma concentrations and analyze tumor tissues for apoptosis markers. The plasma concentration-time profile for Conjugate 1 shows dose-dependent concentrations with i.v. bolus administration at 2.5 and 5.0 mg/kg (12.6 and 32.5 μg/mL, respectively at 24 hours) over the span of sampling times (96 hours) as determined by ELISA for Conjugate 1 and total IgG. Additionally, RT-112 response to Conjugate 1 treatment is detectable in tumor tissues showing a dose-dependent increase in cleaved caspase-3 levels indicating the possible mode of action of the compound.

In the RT-112 studies, Conjugate 1 resulted in a dose dependent significant efficacy resulting in complete response in the majority of the animals and the effect was durable (more than 100 days). Conjugate 1 was significantly more efficacious than Antibody 1, the naked antibody.

Conjugate 1 Efficacy in a UMUC-14 Human Bladder Xenograft Model

In vivo efficacy of Conjugate 1 compared with naked Antibody 1 in UMUC-14 human bladder carcinoma xenografts is genetically distinct from the RT-112 (FGFR3-TACC3) model. UMUC-14 cell lines express approximately 27,000 receptor density as determined by FACS analysis and BANGS and is constitutively active given it harbors the S249C mutation.

Inoculate NOD/SCID Gamma (NSG) mice (female, 5-6 weeks of age) subcutaneously with $5 \times 10^6$ UMUC-14 cells suspended in HBSS. Randomly assign animals into treatment groups, such that the mean tumor volume for each group is 240-250 mm$^3$. Administer Antibody 1 and Conjugate 1 i.v. either 2 doses separated by a 14 day interval or 4 weekly doses. The control uses either conjugate formulation buffer (10 mM Tris, 80 mM NaCl, 3.5% sucrose, 0.01% Tween-20, pH 7.5) or non-targeted chKTI antibodies, chKTI-sulfo-SPDB-DM4 or KLH-sulfo-SPDB-DM4 at 5 mg/kg.

In the first study in the UMUC-14 model, Conjugate 1, at a dose of 5 mg/kg with a dose on day 17 and 31 post tumor implantation, results in a complete regression in 10/10 animals in the UMUC-14 xenograft. The results show that the tumor-free status is maintained for ~15 days. Approximately 30 days after discontinuation of treatment tumor regrowth was observed. Upon retreatment of these tumors on days 78 and 81, Conjugate 1 dosed at 5 mg/kg does not decrease tumor size suggesting the development of tumor resistance.

Both the naked Antibody 1 dosed at 10 mg/kg and the KLH-sulfo-SPDB-DM4 dosed at 5 mg/kg does not significantly affect tumor growth. Plasma Conjugate 1 levels reach ~87 μg/mL at 48 hours post dose, and observe significant increase in cleaved caspase-3 levels as early as 48 hours post administration.

In a second study in the UMUC-14 model, tumor-free status extends significantly following 4 weekly doses of Conjugate 1. Conjugate 1 inhibits UMUC-14 tumor growth in a dose-dependent manner, with 5 mg/kg achieving complete tumor regression in 8 of 8 animals, 2.5 mg/kg reaching tumor stasis and no effect at 1.25 mg/kg. Animals remain tumor free for ~30 days after which tumors start to regrow.

TABLE 9

Summary of UMUC-14 Human Bladder Xenograft Model

| Model | N | Treatment | Total Dose/Schedule | % T/C | Reg. (%) | CR/PR | P Value |
|---|---|---|---|---|---|---|---|
| UMUC-14 (UMUC Study 1) | 10 | Vehicle | 2 (days 17 and 31) | NA | NA | NA | NA |
| | | Antibody 1 (10 mg/kg) | | 65 | NA | NA | 0.15* |
| | | KLH-sulfo-SPDB-DM4 (5 mg/kg) | | 89 | NA | NA | 0.76* |
| | | Conjugate 1 (5 mg/kg) | | NA | 100 | 10/10 CR | <0.0001* |
| UMUC-14 (UMUC Study 2) | 8 | chKTI (5 mg/kg) | 4 (4 weekly doses) | NA | NA | NA | NA |
| | | Antibody 1 (5 mg/kg) | | 71 | NA | NA | 0.28* |
| | | chKTI sulfo-SPDB-DM4 (5 mg/kg) | | 99 | NA | NA | 0.86* |
| | | Conjugate 1 (5 mg/kg) | | 77 | NA | NA | 0.31* |
| | | Conjugate 1 (2.5 mg/kg) | | 13 | NA | 2/8 | <0.0001* |
| | | Conjugate 1 (5.0 mg/kg) | | NA | 100 | 8/8 | <0.0001* |

*Comparison to the Vehicle or chKTI control
NA: Not Applicable

In the UMUC-14 human bladder studies, significant affect achieving 100% CR after repeated i.v. dosing was followed by tumor regrown.

Conjugate 1 Efficacy in BFTC-905 FGFR3 Wild Type (WT) Human Bladder Xenograft Models Determine the efficacy of Conjugate 1 in the presence of wild type FGFR3 expression. Inoculate NOD/SCID Gamma (NSG) subcutaneously with $2\times10^6$ BFTC-905 suspended in HBSS. After randomization, administer Antibody 1 and Conjugate 1 i.v. on a weekly schedule. The control uses either KLH or chKTI antibodies and non-targeted KLH-sulfo-SPDB-DM4 or chKTI-sulfo-SPDB-DM4. In a combination study, administer cisplatin i.p. weekly.

Conjugate 1 treatment exhibits dose-dependent antitumor efficacy in BFTC-905 xenografts achieving tumor stasis at 5 mg/kg, while significantly inhibiting tumor growth at 1.25 and 2.5 mg/kg. The combination of Conjugate 1 and cisplatin results in tumor regressions with 10/10PR, and the effect is significantly greater than each monotherapy. Conjugate 1 shows a trend for increase of tissue cleaved caspase-3 levels.

TABLE 10

Summary of BFTC-905 Human Wild Type Bladder Xenograft Model

| Model | N | Treatment | Total Dose/Schedule | % T/C | Reg. (%) | CR/PR | P Value |
|---|---|---|---|---|---|---|---|
| BFTC-905 (FGFR3 WT Study 1) | 12 | KLH (10mg/kg) | 4 (4 weekly doses) | NA | NA | NA | NA |
| | | Antibody 1 (10 mg/kg) | | 83 | NA | NA | 0.37* |
| | | KLH-sulfo-SPDB-DM4 (5 mg/kg) | 5 (5 weekly doses) | 18 | NA | NA | <0.0001* |
| | | Conjugate 1 (5 mg/kg) | | NA | 16 | NA | <0.0001* |
| | | chKTI (5 mg/kg) | | NA | NA | NA | NA |
| | | Antibody 1 (5 mg/kg) | | 95 | NA | NA | 0.71* |
| BFTC-905 (FGFR3 WT Study 2) | 8 | chKTI sulfo-SPDB-DM4 (5 mg/kg) | 4 (4 weekly doses) | 2 | NA | NA | <0.0001* |
| | | Conjugate 1 (1.25 mg/kg) | | 58 | NA | NA | 0.005* |
| | | Conjugate 1 (2.5 mg/kg) | | 21 | NA | NA | <0.0001* |

TABLE 10-continued

Summary of BFTC-905 Human Wild Type Bladder Xenograft Model

| Model | N | Treatment | Total Dose/ Schedule | % T/C | Reg. (%) | CR/PR | P Value |
|---|---|---|---|---|---|---|---|
| | | Conjugate 1 (5.0 mg/kg) | | NA | −23 | 1/8 CR 1/8 PR | <0.0001* |
| BFTC-905 (FGFR3 WT | | chKTI (5 mg/kg) | 4 (4 weekly doses) | NA | NA | NA | NA |
| | | Conjugate 1 (5.0 mg/kg) | | 7 | NA | 1/10PR | <0.0001* |
| | | Cisplatin (4 mg/kg) | | 69 | NA | 0/10 | <0.05* |
| | | Conjugate 1 + Cisplatin | | NA | 67 | 10.10 | <0.0001* <0.0001** |

*Comparison to the chKTI or KLH control
**Comparison to cisplatin and Conjugate 1
NA: Not Applicable In BFTC-905, human wild type FGFR3 bladder xenograft cell lines express approximately 11,000 receptor density as determined by FACS analysis and BANGS. Conjugate 1 only achieved tumor stasis at the higher doses tested. In combination with cisplatin, the combination therapy of Conjugate 1 and cisplatin significantly improves the effects of Conjugate 1 alone, resulting in tumor regression with 10/10 PR. The combination effect is more than additive as defined by the Bliss Independence Method.

Conjugate 1 Efficacy in KU-19-19 FGFR3 Negative Human Bladder Xenograft Models

Evaluate Conjugate 1 in a FGFR3 negative bladder carcinoma xenograft model, KU-19-19, to establish the specificity of Conjugate 1. Briefly, inoculate Nu/nu (female, 5-6 weeks of age) subcutaneously with KU-19-19 cells at $2 \times 10^6$ cells/mouse suspended in HBSS. After randomization, administer Antibody 1 and Conjugate 1 i.v. on a weekly schedule. The control uses chKTI antibodies and non-targeted chKTI-sulfo-SPDB-DM4.

TABLE 11

Summary of KU-19-19 FGFR3 Negative Human Bladder Xenograft Model

| Model | N | Treatment | Total Dose/Schedule | % T/C | Reg. (%) | CR/PR | P Value |
|---|---|---|---|---|---|---|---|
| KU-19-19 | 8 | chKTI (5 mg/kg) | 2 (2 weekly doses) | NA | NA | NA | NA |
| | | Antibody 1 (5 mg/kg) | | 79 | NA | NA | >0.05* |
| | | chKTI-sulfo-SPDB-DM4 (5 mg/kg) | | 91 | NA | NA | >0.05* |
| | | Conjugate 1 (5 mg/kg) | | 89 | NA | NA | >0.05* |

*Comparison to the chKTI control
NA: Not Applicable

As expected, Conjugate 1 dosed at 5 mg/kg on a weekly schedule exhibits no antitumor effect against KU-19-19 tumors, indicating the specificity of the test article towards FGFR3 antigen. Likewise, the naked antibody (Antibody 1) and chKTI-sulfoSDPD-DM4, both dosed weekly at 5 mg/kg, exhibited no antitumor activity.

Conjugate 1 Efficacy in a KMS-11 Human Multiple Myeloma Xenograft Model

Evaluate the in vivo efficacy of Conjugate 1 in KMS-11 and KMS-11LP (luciferase positive) human multiple myeloma (MM) xenograft models. KMS-11 expresses high levels of FGFR3 (~120,000) and carries both a chromosomal translocation (t(4;14)) and a single point mutation, Y373C. KMS-11LP is a derivative of the parental KMS-11 line that is luciferase positive and expresses higher levels of FGFR3 antigen (~159,000).

Inoculate NOD/SCID Gamma (NSG) mice (female, 5-6 weeks of age) subcutaneously with $10 \times 10^6$ KMS-11 or KMS-11LP cells suspended in HBSS. When tumors reach a mean tumor volume of ~300 mm$^3$, randomly assign the animals into treatment groups. Administer Antibody 1 and Conjugate 1 i.v. either once, weekly or every other week. The control uses either conjugate formulation buffer (10 mM Tris, 80 mM NaCl, 3.5% sucrose, 0.01% Tween-20, pH 7.5) or non-targeted KLH antibody and KLH-sulfo-SPDB-DM4.

In KMS-11 study 1, treatment with a single dose of Conjugate 1 significantly inhibits the growth of KMS-11 tumors with initial tumor stasis followed by tumor regrowth. Analyses of collected tumor tissues indicates significant increase in cleaved caspase-3 levels that starts 12 hours post dose and peaks at 24 hours.

Conjugate 1 efficacy improves significantly with a more aggressive dosing schedule. In KMS-11 study 3, a total of 5 weekly doses of Conjugate 1 results in complete response in 2 of 7 animals while 5 of 7 animals achieve partial response. There is however significant effect with non-targeted conjugate control with this dosing schedule.

TABLE 12

Summary of KMS-11 Human Multiple Myeloma Xenograft Model

| Model | N | Treatment | Total Dose/Schedule | % T/C | Reg. (%) | CR/PR | P Value |
|---|---|---|---|---|---|---|---|
| KMS-11 (MM) (KMS-11 Study 1) | 10 | Vehicle | 1 (day 19) | NA | NA | NA | NA |
| | | Antibody 1 (10 mg/kg) | | 75 | NA | NA | 0.02* |
| | | KLH-sulfo-SPDB-DM4 (5 mg/kg) | | 70 | NA | NA | 0.002* |
| | | Conjugate 1 (5 mg/kg) | | 30 | NA | NA | <0.0001* |
| KMS-11 LP (KMS-11 Study 2) | 10 | Vehicle | 2 (days 20 and 34) | NA | NA | NA | NA |
| | | Antibody 1 (10 mg/kg) | | 63 | NA | NA | 0.03* |
| | | KLH-sulfo-SPDB-DM4 (5 mg/kg) | | 25 | NA | NA | <0.0001* |
| | | Conjugate 1 (5 mg/kg) | 3 (days 20, and 48) | NA | 39 | 10/10 | <0.0001* |
| KMS-11 (MM) (KMS-11 Study 3) | 12 | KLH (10 mg/kg) | 3 (3 weekly doses) | NA | NA | NA | NA |
| | | Antibody 1 (10 mg/kg) | 5 (5 weekly doses) | 52 | NA | NA | 0.01* |
| | | KLH-sulfo-SPDB-DM4 (5 mg/kg) | | 12 | NA | 1/7 PR | <0.0001* |
| | | Conjugate 1 (5 mg/kg) | | NA | 40 | 2/7 CR, 5/7 PR | <0.0001* |

*Comparison to the Vehicle or KLH control
NA: Not Applicable

The studies show significant robust efficacy in the Conjugate 1 treated KMS-11LP xenograft that expresses slightly higher antigen density (152,000) compared to parental KMS-11 (119,000). Conjugate 1 treatment results in complete response in 10 of 10 animals after a total of 3 doses administered every 14 days and tumor free status is maintained during the observation period Day 70.

| ADDITIONAL SEQUENCES |
|---|
| SEQ ID NO 11 |
| MGAPACALALCVAVAIVAGASSESLGTEQRVVGRAAEVPGPEPGQELVFGSGDAVE LSCPPPGGGPMGPTVWVKDGTGLVPSERVLVGPQRLVLNASHEDSGAYSCRQRLTR VLCHFSVRVTDAPSSGDDEDGEDEAEDTGVDTGAPYWTRPERMDKKLLAVPAANT VRFRCPAAGNPTPSISWLKNGREFRGEHRIGGIKLRQQWSLVMESVVPSDRGNYTCV VENKFGSIRQTYTLDVLERSPHRPILQAGLPANQTAVLGSDVEFHCKVYSDAPHIQW LKHVEVNGSKVGPDGTPYVTVLKTAGANTTDKELEVLSLHNVTFEDAGEYTCLAG NSIGFSHHSAWLVVLPAEEELVEADEAGSVYAGILSYGVGFFLFILVVAAVTLCRLRS PPKKGLGSPTVHKISFPLKRQVSLESNASNSSNTPLVRIARLSSGEGPTLANVSELELP ADPKWELSRARLTLGKPLGEGCFGQVVMAEAIGIDKDRAAKPVTVAVKMLKDDAT DKDLSDLVSEMEMMKMIGKHKNIINLLGACTQGGPLYVLVEYAAKGNLREFLRAR RPPGLDYSFDTCKPPEEQLTFKDLVSCAYQVARGMEYLASKCIHRDLAARVLVTED NVMKIADFGLARDVHNLDYYKKTTNGRLPVKWMAPEALFDRVYTHSDVSFGVLL WEIFTLGGSPYPGIPVEELFKLLKEGHRMDKPANCTHDLYMIMRECWHAAPSRPTFK LVEDLDRVLTVTSTDEYLDLSAPFEYSPGGQDTPSSSSSGDDSVFAHDLLPPAPPSSG GSRT |
| SEQ ID NO 12 |
| gaggtccagctggtacagtctggagctgaggtgaagaagcctggggcctcagtgaaagtctcc tgcaaggcttctggctacatgttaccagctatgggatcagttgggtgcgacaggcccct |

```
ggacaagggcttgagtggatgggatgggtcagcacttacaatggtgacacaaactatgcg
cagaagttccagggcagagtcaccgtgaccacagacacatccacgagcacagcctacatg
gagctgaggagcctgagatctgaggacacggccgtgtattactgtgcgagagtcttggga
tactatgatagtatagatggctactacacggtatggacgtctggggccaagggaccacg
gtcaccgtctcaagcgctagcaccaagggcccatcggtcttccccctggcaccctcctcc
aagagcacctctgggggcacagcggccctgggctgcctggtcaaggactacttccccgaa
ccggtgacggtgtcgtggaactcaggcgccctgaccagcggcgtgcacaccttcccggct
gtcctacagtcctcaggactctactccctcagcagcgtggtgaccgtgccctccagcagc
ttgggcacccagacctacatctgcaacgtgaatcacaagcccagcaacaccaaggtggac
aagagagttgagcccaaatcttgtgacaaaactcacacatgcccaccgtgcccagcacct
gaactcctggggggaccgtcagtcttcctcttccccccaaaacccaaggacaccctcatg
atctcccggacccctgaggtcacatgcgtggtggtggacgtgagccacgaagaccctgag
gtcaagttcaactggtatgtggacggcgtggaggtgcataatgccaagacaaagccgcgg
gaggagcagtacaacagcacgtaccgtgtggtcagcgtcctcaccgtcctgcaccaagac
tggctgaatggcaaggagtacaagtgcaaggtctccaacaaagcccteecageccceate
gagaaaaccatctccaaagccaaagggcagccccgagaaccacaggtgtacaccctgccc
ccatcccgggaggagatgaccaagaaccaagtcagcctgacctgcctggtcaaaggcttc
tatcccagcgacatcgccgtggagtgggagagcaatgggcagccggagaacaactacaag
accacgcctcccgtgctggactccgacggctccttcttcctctattccaagctcaccgtg
gacaagagcaggtggcagcaggggaacgtcttctcatgctccgtgatgcatgaggctctg
cacaaccactacacgcagaagagcctctccctgtctccgggcaaa
```

```
                                                    SEQ ID NO 13
cagtctgtgctgactcagccacccctcactgtcagtggccccaggaaagacggccacctttacc
tgtgggggaaacaacattggagacaagagtgttcactggtaccggcagaagccaggccag
gcccctgtcctggtcatgtatcttgataccgaacggccctcagggatccctgagcgaatg
tctggctccaactttggggaacacggccaccctgacgatcaccagggtcgaagccgggat
gaggccgactattactgtcaggtgtgggatagtggtagtgatcatgtggtcttcggcgga
gggaccaagctgaccgtcctaggtcagcctaaggctgccccctcggtcactctgttcccg
ccctcctctgaggagcttcaagccaacaaggccacactggtgtgtctcataagtgacttc
tacccgggagccgtgacagtggcctggaaggcagatagcagccccgtcaaggcgggagtg
gagaccaccaccctccaaacaaagcaacaacaagtacgcggccagcagctacctgagc
ctgacgcctgagcagtggaagtcccacagaagctacagctgccaggtcacgcatgaaggg
agcaccgtggagaagacagtggcccctgcagaatgctct
```

We claim:

1. A compound of Formula I:

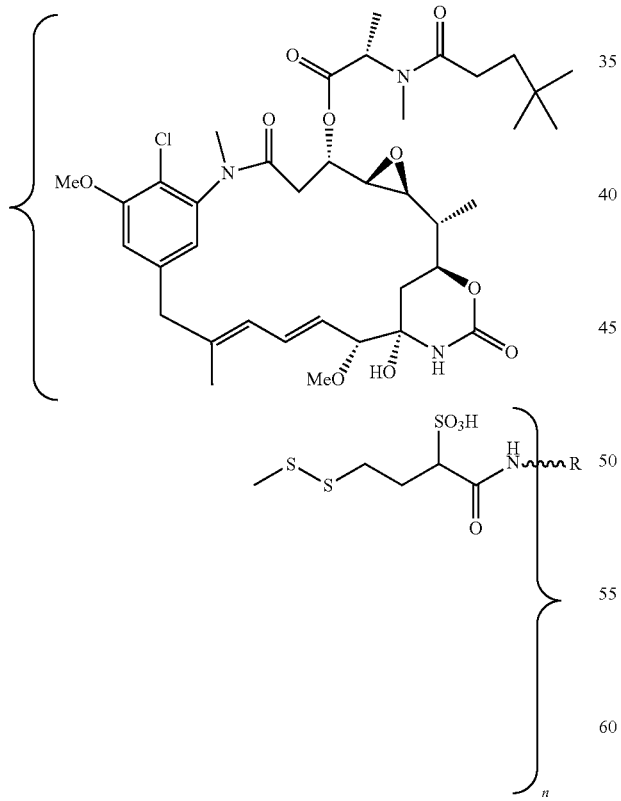

wherein n is an integer from 1-10 and wherein R is a cell binding agent that binds to human FGFR3 (SEQ ID NO 11) and comprises a CDRH1 having the sequence GYMFTSYGIS (SEQ ID NO 1), a CDRH2 having the sequence WVSTYNGDTNYAQKFQG (SEQ ID NO 2), a CDRH3 having the sequence VLGYYDSIDGYYYG-MDV (SEQ ID NO 3), a CDRL1 having the sequence GGNNIGDKSVH (SEQ ID NO 4), a CDRL2 having the sequence LDTERPS (SEQ ID NO 5), and a CDRL3 having the sequence QVWDSGSDHVV (SEQ ID NO 6).

2. The compound of claim 1, wherein the cell binding agent further comprises a variable heavy (VH) amino acid sequence of:

(SEQ ID NO 7)
EVQLVQSGAEVKKPGASVKVSCKASGYMFTSYGISWVRQAPGQGLEWMGW

VSTYNGDTNYAQKFQGRVTVTTDTSTSTAYMELRSLRSEDTAVYYCARVL

GYYDSIDGYYYGMDVWGQGTTVTVSS;

and a variable light (VL) amino acid sequence of:

(SEQ ID NO 8)
QSVLTQPPSLSVAPGKTATFTCGGNNIGDKSVHWYRQKPGQAPVLVMYLD

TERPSGIPERMSGSNFGNTATLTITRVEAGDEADYYCQVWDSGSDHVVFG

GGTKLTVLG.

3. The compound of claim 2, wherein the cell binding agent further comprises: a light chain comprising the amino acid sequence of SEQ ID NO: 10; and a heavy chain comprising the amino acid sequence of SEQ ID NO: 9.

4. The compound of claim 3, wherein the cell binding agent further comprises: two light chains each comprising the amino acid sequence of SEQ ID NO: 10; and two heavy chains each comprising the amino acid sequence of SEQ ID NO: 9.

5. The compound of claim 4, wherein n is 2.0 to 5.0.

6. The compound of claim 5, wherein n is 3.5±0.5.

7. A pharmaceutical composition comprising the compound of claim 4 together with a pharmaceutically acceptable carrier, diluent or excipient.

8. A pharmaceutical composition comprising the compound of claim 5 together with a pharmaceutically acceptable carrier, diluent or excipient.

9. A pharmaceutical composition comprising the compound of claim 6 together with a pharmaceutically acceptable carrier, diluent or excipient.

10. The pharmaceutical composition of claim 7, further comprising an additional pharmaceutical agent.

11. The pharmaceutical composition of claim 8, further comprising an additional pharmaceutical agent.

12. The pharmaceutical composition of claim 9, further comprising an additional pharmaceutical agent.

13. A method of treating cancer in a mammal, comprising administering to said in need thereof the compound of claim 4, wherein the cancer is selected from the group consisting of bladder cancer or multiple myeloma.

14. A method of treating cancer in a mammal, comprising administering to said in need thereof the compound of claim 5, wherein the cancer is selected from the group consisting of bladder cancer or multiple myeloma.

15. The method of claim 13, further comprising administering another anti-cancer treatment to said mammal, wherein said anti-cancer treatment is selected from the group consisting of an anti-angiogenic agent, a chemotherapeutic agent, and an anti-neoplastic agent.

16. The method of claim 15, wherein said anti-neoplastic agent is cisplatin.

17. A method of treating cancer in a patient, comprising the steps:
   (a) measuring the expression level of FGFR3 (SEQ ID NO 11) in a sample taken from the patient, wherein the sample is selected from the group consisting of blood, serum, plasma, urine, and tissue, and
   (b) administering to the patient the compound of claim 4, if the FGFR3 expression level is above the FGFR3 expression level found in a control population.

18. A method of treating cancer in a patient, comprising the steps:
   (a) determining the presence of an anomaly in a sample taken from the patient, wherein the sample is selected from the group consisting of blood, serum, plasma, urine, tissue, tumor cells, tumor tissue samples, circulating tumor cells, and circulating DNA, and wherein the anomaly is:
      (1) a mutation of FGFR3 (SEQ ID NO 11), wherein the mutation is selected from the group consisting of S249C, R248C, Y373C, Y375C, and combinations thereof,
      (2) a fusion of FGFR3-TACC3, or
      (3) a combination of (1) and (2), and
   (b) administering to the patient the compound according to claim 4 if the anomaly is present.

* * * * *